US011667661B2

(12) United States Patent
Kim et al.

(10) Patent No.: US 11,667,661 B2
(45) Date of Patent: Jun. 6, 2023

(54) BENZIMIDAZOLE DERIVATIVES, PREPARATION METHOD THEREOF AND USE THEREOF AS ANTI-CANCER AGENT COMPRISING THE SAME

(71) Applicant: BIOMETRIX TECHNOLOGY INC, Chuncheon-si (KR)

(72) Inventors: Taisun Kim, Chuncheon-si (KR); Keumsoo Song, Chuncheon-si (KR); Junghun Kim, Seoul (KR)

(73) Assignee: BIOMETRIX TECHNOLOGY INC, Chuncheon-si (KR)

( * ) Notice: Subject to any disclaimer, the term of this patent is extended or adjusted under 35 U.S.C. 154(b) by 0 days.

(21) Appl. No.: 17/195,425

(22) Filed: Mar. 8, 2021

(65) Prior Publication Data
US 2021/0300959 A1    Sep. 30, 2021

(30) Foreign Application Priority Data

Mar. 30, 2020   (KR) .................. 10-2020-0038673
Sep. 28, 2020   (KR) .................. 10-2020-0125942

(51) Int. Cl.
*C07H 15/26*   (2006.01)
*A61P 35/00*   (2006.01)

(52) U.S. Cl.
CPC .............. *C07H 15/26* (2013.01); *A61P 35/00* (2018.01)

(58) Field of Classification Search
None
See application file for complete search history.

(56) References Cited

U.S. PATENT DOCUMENTS

| | | |
|---|---|---|
| 6,455,507 B1 | 9/2002 | Drach et al. |
| 11,025,206 B2 | 6/2021 | Xia et al. |
| 11,028,055 B2 | 6/2021 | Zetter et al. |
| 2002/0094963 A1 | 7/2002 | Drach et al. |
| 2019/0190467 A1 | 6/2019 | Xia et al. |
| 2020/0199078 A1 | 6/2020 | Zetter et al. |
| 2022/0055993 A1 | 2/2022 | Zetter et al. |

FOREIGN PATENT DOCUMENTS

| | | |
|---|---|---|
| JP | 2002-504105 A | 2/2002 |
| WO | WO 98/51304 | 11/1998 |
| WO | WO 98/56761 | 12/1998 |
| WO | WO 2005/058870 A1 | 6/2005 |
| WO | WO 2017/095950 A2 | 6/2017 |
| WO | WO 2019/157338 A1 | 8/2019 |

OTHER PUBLICATIONS

Blagosklonny, et al., "Carcinogenesis, cancer therapy and chemoprevention," Cell Death and Differentiation, vol. 12, 2005, pp. 592-602.
Introduction and treatment trends of chemotherapy, BRIC View 2016-T20, OncometPlus Pharmaceuticals Co., Ltd, with English translation, 40 pp.
Incurix Jeong kyung-chae, "Myc Inhibitor Development Trends," with English translation, 41 pp.
Devita, Jr., et al., "A History of Cancer Chemotherapy," Cancer Res 2008; 68: (21), AACR Centennial Series, pp. 8643-8653.
Housman et al., "Druo Resistance in Cancer: An Overview," Cancers, vol. 6, 2014, pp. 1769-1792.
Zhou, et al., "Targeting Microtubules tor Cancer Chemotherapy," Curr. Med. Chem.—Anti-Cancer Agents, vol. 5, No. 1, 2005, 7 pages.
Mikula-Pietrasik, et al., "Comprehensive review on how platinum- and taxane-based chemotherapy of ovarian cancer affects biology of normal cells," Cellular and Molecular Life Sciences, vol. 76, No. 4, 2019, pp. 681-897.
Kumar, et al., "Potential anticancer role of colchicine-based derivatives: an overview," Anti-Cancer Drugs, vol. 28, No. 3, 2017, pp. 250-262.
Pryor, et al., "The Microtubule Stabilizing Agent Laulimalide Does Not Bind in the Taxoid Site, Kills Cells Resistant to Paclitaxel and Epothilones, and May Not Require its Epoxide Moiety for Activity," Biochemistry, vol. 41, 2002, pp. 9109-9115.
Ravelli, et al., "Insight into tubulin regulation from a complex with colchicine and a stathmin-like domain," Nature, vol. 428, Mar. 2004, pp. 198-202.
Mikula-Pietrasik et al., "Comprehensive review on how platinum- and taxane-based chemotherapy of ovarian cancer affects biology of normal cells," Cellular and Molecular Life Sciences, vol. 76, No. 4, 2019, pp. 681-697.
Velasco, et al., "Taxane-Induced Peripheral Neurotoxicity," Toxics, 2015, 28, 3(2), pp. 152-169.
Dogra, et al., "Fenbendazole acts as a moderate microtubule destabilizing agent and causes cancer cell death by modulating multiple cellular pathways," Scientific Reports, vol. 8, No. 1, 11926, Aug. 9, 2018, 15 pages.
Düwel, "Fenbendazole. II. Biological Properties and Activity," Pestic. Sci., vol. 8, 1977, pp. 550-555.

(Continued)

*Primary Examiner* — Traviss C Mcintosh, III
(74) *Attorney, Agent, or Firm* — Lewis Roca Rothgerber Christie LLP

(57) ABSTRACT

According to the present invention, there are provided a benzimidazole carbamate-sugar compound conjugate compound represented by the following Chemical Formula 1, a preparation method thereof, and a use thereof as an anti-cancer agent:

[Chemical Formula 1]

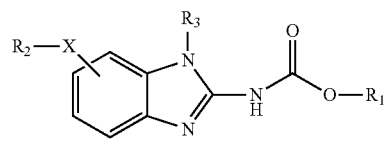

Wherein, $R_1$, $R_2$, $R_3$ and X are as defined in the specification and claims.

11 Claims, 3 Drawing Sheets

(56) References Cited

OTHER PUBLICATIONS

Kawamura et al., "Expression of Glucose Transporter-1 in Human Gastric Carcinoma," Cancer, vol. 92, No. 3, Aug. 1, 2001 American Cancer Society, pp. 634-641.
Fletcher et al., "A Comparison or the Diagnostic Accuracy of $^{18}$F-FDG PET and CT in the Characterization of Solitary Pulmonary Nodules," The Journal of Nuclear Medicine, vol. 49, No. 2, Feb. 2008, pp. 179-185.
Liberti et al., "The Warburg Effect: How Does it Benefit Cancer Cells?" Trends in Biochemical Sciences, vol. 42, No. 3, Mar. 2016, pp. 211-218.
Adekola et al., "Glucose transporters in cancer metabolism," Current Opinion Oncology, vol. 24, No. 6, Nov. 2012, pp. 650-654.
Ancey et al., "Glucose transporters in cancer-from tumor cells to the tumor microenvironment," The FEBS Journal 285, 2018, pp. 2926-2943.
Airley et al., "Glucose Transporter Glut-1 Expression Correlates with Tumor Hypoxia and Predicts Metastasis-free Survival in Advanced Carcinoma of the Cervix[1]," Clinical Cancer Research, vol. 7, Apr. 2001, pp. 928-934.
Brice, et al., "Advanced Hodgkin Disease with Large Mediastinal Involvement Can Be Treated with Eight Cycles of Chemotherapy Alone after a Major Response to Six Cycles of Chemotherapy," Cancer, vol. 92, No. 3, Aug. 1, 2001.
Aguayo-Ortiz, et al., "Structure-based approaches for the design of benzimidazole-2-carbamate derivatives as tubulin polymerization inhibitors," Chem Biol Drug Des., vol. 90, No. 1, 2017, pp. 40-51.
Chu, et al., "Potent Inhibition of Tubulin Polymerisation and Proliferation of Paclitaxel-resistant 1A9PTX22 Human Ovarian Cancer Cells by Albendazole," Anticancer Research, 29, 2009, pp. 3791-3796.
Quan, et al., "Gluscose-modification of cisplatin to facilitate cellular uptake, mitigate toxicity to normal cells, and improve anti-cancer effect in cancer cells," Journal of Molecular Structure 1203 (2020) 127361, 5 pages.
Zhang, et al., "Anthelmintic drug albendazole arrests human gastric cancer cells at the mitotic phase and induces apoptosis," Experimental and Therapeutic Medicine 13, 2017, pp. 595-603.
Jevtić, et al., "Adverse effects of longterm, continual administration of high doses of albendazole in the treatment of ecinococcal disease," Vojnosanitetski Pregled, vol. 65, No. 7, Jul. 2008, pp. 539-544, English Abstract.
Thaker, et al., "Viral hijacking of cellular metabolism," BMC Biology, vol. 17, No. 59, 2019, 15 pages.
Fontaine, et al., "Dengue Virus Induces and Requires Glycolysis for Optimal Replication," Journal of Virology, vol. 89, No. 4, Feb. 2015, pp. 2358-2366.
Kohio, et al., "Glycolytic control of vacuolar-type ATPase activity: A mechanism to regulate influenza viral infection," Virology 444, 2013, pp. 301-309.
Gomes, et al., "Synthetic acylsugars and their effects on the control of arthropod pests," Ciencia e Agrotecnologia 41(2), pp. 201-208, Mar./Apr. 2017.
Collins, "Saturated and unsaturated lactones," J. Chem. Soc., Perkin Trans. 1, 1998, pp. 1869-1888.
Hennen, et al., "Enzymes in Carbohydrate Synthesis: Lipase-Catalyzed Selective Acylation and Deacylation of Furanose and Pyranose Derivatives," J. Org. Chem., vol. 53, No. 21, 1988, pp. 4939-4945.
Slater et al., "Studies on Succinate-Tetrazolium Reductase Systems III. Points of Coupling of Four Different Tetrazolium Salts," Biochem. Biophys. Acta, 77, 1963, pp. 383-393.
Van De Loosdrecht, et al., "A tetrazolium-based colorimetric MTT assay to quantitate human monocyte mediated cytotoxicity against leukemic cells from cell lines and patients with acute myeloid leukemia," Journal of Immunological Methods, 174, 1994, pp. 311-320.
Alley, et al., "Feasibility of Drug Screening with Panels of Human Tumor Cell Lines Using a Microculture Tetrazolium Assay[1]," Cancer Research 48, pp. 589-601, Feb. 1, 1988.
Office Action for Japanese Patent Application No. 2021-031662, dated Feb. 22, 2022, 8 pages.
Korean Office Action for Application No. 10-2020-0125942, dated Sep. 5, 2022, with English translation, 14 pages.
Jae Eun Cheong et al., "Synthesis and anticancer activity of novel water soluble benzimidazole carbamates", European Journal of Medicinal Chemistry 144 (2018) pp. 372-385.

FIG. 3

| Structure | 1H NMR |
|---|---|
| (structure) | 1H NMR (400 MHz, DMSO-d6): δ = 11.62 (s, 1H), 7.42 (s, 1H), 7.32 (d, J = 7.49Hz, 1H), 7.09 (d, J = 7.50Hz, 1.46Hz, 1H), ), 5.04 (d, J = 7.2 Hz, 1H), 3.99–3.90 (m, 1H), , 3.80–3.71 (m, 1H), 3.62–3.32 (m, 4H), 2.58 (t, J = 7.14, 4.48Hz, 2H), 1.54 (m, 2H), 0.95 (t, J = 7.96Hz, 3H), |
| (structure) | 1H NMR (400 MHz, DMSO-d6): δ = 11.62 (s, 1H), 7.42 (s, 1H), 7.32 (d, J = 7.49Hz, 1H), 7.09 (d, J = 7.50Hz, 1.46Hz, 1H), 5.34 (d, 1H), 5.25 (d, 1H), 5.05(t, 1H), 3.88–3.92 (s, 2H), 3.99–3.90 (m, 1H), , 3.80–3.71 (m, 1H), 3.62–3.32 (m, 4H), 2.58 (t, J = 7.14, 4.48Hz, 2H), 1.54 (m, 2H), 0.95 (t, J = 7.96Hz, 3H) |
| (structure) | 1H NMR (400 MHz, DMSO-d6): δ = 11.62 (s, 1H), 7.42 (s, 1H), 7.32 (d, J = 7.49Hz, 1H), 7.09 (d, J = 7.50Hz, 1.46Hz, 1H), 5.04 (d, J = 7.2 Hz, 1H), 3.25–3.33 and 3.54–3.62 (m, 2H), 3.70–4.15(m, 4H), 2.58 (t, J = 7.14, 4.48Hz, 2H), 1.54 (m, 2H), 0.95 (t, J = 7.96Hz, 3H), |
| (structure) | 1H NMR (400 MHz, DMSO-d6): δ = 11.62 (s, 1H), 7.42 (s, 1H), 7.32 (d, J = 7.49Hz, 1H), 7.09 (d, J = 7.50Hz, 1.46Hz, 1H), 5.04 (d, J = 7.2 Hz, 1H), 3.25–3.33 and 3.54–3.62 (m, 2H), 3.70–4.15(m, 4H), 2.58 (t, J = 7.14, 4.48Hz, 2H), 1.54 (m, 2H), 0.95 (t, J = 7.96Hz, 3H), |

FIG. 4

| Structure | 1H NMR |
|---|---|
| (structure) | 1H NMR (400 MHz, DMSO-d6): δ = 11.62 (s, 1H), 7.42 (s, 1H), 7.32 (d, J = 7.49Hz, 1H), 7.09 (d, J = 7.50Hz, 1.46Hz, 1H), 5.04 (d, J = 7.2 Hz, 1H), 3.99–3.90 (m, 1H), , 3.80–3.71 (m, 1H), 3.62–3.32 (m, 4H), 2.58 (t, J = 7.14, 4.48Hz, 2H), 1.54 (m, 2H), 0.95 (t, J = 7.96Hz, 3H), |
| (structure) | 1H NMR (400 MHz, DMSO-d6): δ = 11.62 (s, 1H), 7.42 (s, 1H), 7.32 (d, J = 7.49Hz, 1H), 7.10 (d, J = 7.50Hz, 1.46Hz, 1H), 5.33 (d, 1H), 5.24 (d, 1H), 5.06(t, 1H) 3.88–3.94 (s, 2H), 3.99–3.91 (m, 1H), , 3.80–3.74 (m, 1H), 3.62–3.33 (m, 4H), 2.57 (t, J = 7.14, 4.48Hz, 2H), 1.53 (m, 2H), 0.94 (t, J = 7.96Hz, 3H) |
| (structure) | 1H NMR (400 MHz, DMSO-d6): δ = 11.62 (s, 1H), 7.42 (s, 1H), 7.32 (d, J = 7.49Hz, 1H), 7.09 (d, J = 7.50Hz, 1.46Hz, 1H), 5.04 (d, J = 7.2 Hz, 1H), 3.25–3.33 and 3.54–3.62 (m, 2H), 3.70–4.15(m, 4H), 2.58 (t, J = 7.14, 4.48Hz, 2H), 1.54 (m, 2H), 0.95 (t, J = 7.96Hz, 3H) |
| (structure) | 1H NMR (400 MHz, DMSO-d6): δ = 11.62 (s, 1H), 7.42 (s, 1H), 7.32 (d, J = 7.49Hz, 1H), 7.09 (d, J = 7.50Hz, 1.46Hz, 1H), 5.04 (d, J = 7.2 Hz, 1H), 3.25–3.33 and 3.54–3.62 (m, 2H), 3.70–4.15(m, 4H), 2.58 (t, J = 7.14, 4.48Hz, 2H), 1.54 (m, 2H), 0.95 (t, J = 7.96Hz, 3H) |
| (structure) | 1H NMR (400 MHz, DMSO-d6): δ = 11.62 (s, 1H), 7.42 (s, 1H), 7.32 (d, J = 7.49Hz, 1H), 7.09 (d, J = 7.50Hz, 1.46Hz, 1H), 5.04 (d, J = 7.2 Hz, 1H), 3.99–3.90 (m, 1H), , 3.80–3.71 (m, 1H), 3.62–3.32 (m, 3H), 2.58 (t, J = 7.14, 4.48Hz, 2H), 1.54 (m, 2H), 0.95 (t, J = 7.96Hz, 3H) |

FIG. 5

| Structure | 1H NMR |
|---|---|
| (structure) | 1H NMR (400 MHz, DMSO-d6): δ = 12.1 (s, 1H), 11.0 (s, 1H), 7.38 (m, J = Hz, 8H) 5.04 (d, J = 7.2 Hz, 1H), 3.99-3.90 (m, 1H), , 3.80-3.71 (m, 1H), 3.62-3.32 (m, 4H) |
| (structure) | 1H NMR (400 MHz, DMSO-d6): δ = 12.1 (s, 1H), 11.0 (s, 1H), 7.38 (m, J = Hz, 8H) 3.88-3.92 (s, 2H), 3.99-3.90 (m, 1H), , 3.80-3.71 (m, 1H), 3.62-3.32 (m, 4H) |
| (structure) | 1H NMR (400 MHz, DMSO-d6): δ = 12.1 (s, 1H), 11.0 (s, 1H), 7.38 (m, J = Hz, 8H) 5.04 (d, J = 7.2 Hz, 1H), 3.25-3.33 and 3.54-3.62 (m, 2H), 3.70-4.15(m, 4H) |
| (structure) | 1H NMR (400 MHz, DMSO-d6): δ = 12.1 (s, 1H), 11.0 (s, 1H), 7.38 (m, J = Hz, 8H) 5.04 (d, J = 7.2 Hz, 1H), 3.25-3.33 and 3.54-3.62 (m, 2H), 3.70-4.15(m, 4H) |

FIG. 6

| Structure | 1H NMR |
|---|---|
| (structure) | 1H NMR (400 MHz, DMSO-d6): δ = 12.1 (s, 1H), 11.0 (s, 1H), 7.38 (m, J = Hz, 8H) 5.04 (d, J = 7.2 Hz, 1H), 3.99-3.90 (m, 1H), , 3.80-3.71 (m, 1H), 3.62-3.32 (m, 4H) |
| (structure) | 1H NMR (400 MHz, DMSO-d6): δ = 12.1 (s, 1H), 11.0 (s, 1H), 7.38 (m, J = Hz, 8H) 3.88-3.92 (s, 2H), 3.99-3.90 (m, 1H), , 3.80-3.71 (m, 1H), 3.62-3.32 (m, 4H) |
| (structure) | 1H NMR (400 MHz, DMSO-d6): δ = 12.1 (s, 1H), 11.0 (s, 1H), 7.38 (m, J = Hz, 8H) 5.04 (d, J = 7.2 Hz, 1H), 3.25-3.33 and 3.54-3.62 (m, 2H), 3.70-4.15(m, 4H) |
| (structure) | 1H NMR (400 MHz, DMSO-d6): δ = 12.1 (s, 1H), 11.0 (s, 1H), 7.38 (m, J = Hz, 8H) 5.04 (d, J = 7.2 Hz, 1H), 3.25-3.33 and 3.54-3.62 (m, 2H), 3.70-4.15(m, 4H) |
| (structure) | 1H NMR (400 MHz, DMSO-d6): δ = 12.1 (s, 1H), 11.0 (s, 1H), 7.38 (m, J = Hz, 8H) 5.04 (d, J = 7.2 Hz, 1H), 3.99-3.90 (m, 1H), , 3.80-3.71 (m, 1H), 3.62-3.32 (m, 3H) |

BENZIMIDAZOLE DERIVATIVES, PREPARATION METHOD THEREOF AND USE THEREOF AS ANTI-CANCER AGENT COMPRISING THE SAME

CROSS-REFERENCE TO RELATED APPLICATIONS

This application claims the priority of Korean Patent Application No. 10-2020-0038673 filed on Mar. 30, 2020 and Korean Patent Application No. 10-2020-0125942 filed on Sep. 28, 2020 in the Korean Intellectual Property Office, the disclosure of which is incorporated herein by reference.

BACKGROUND OF THE INVENTION

Field of the Invention

The present invention relates to novel benzimidazole derivatives, a preparation method thereof, and a use thereof as an anti-cancer agent.

Description of the Related Art

Benzimidazole is a compound in which an imidazole ring is attached to a benzene ring, and has a variety of bioactivities and physiological effects, and is attracting attention as mother nuclei of various drugs. Compounds having such a benzimidazole structure have been reported to exhibit effects on various diseases depending on a substituent, and have been developed as, for example, anti-inflammatory analgesics, antifungal agents, anti-cancer agents, anthelmintics, antihistamines, and the like.

The benzimidazole has a property of inhibiting the formation of microtubules in many papers (see Chem Biol Drug Des., 2017 July; 90(1):40-51; Scientific REPORTS, 2018, 8:11926; and ANTICANCER RESEARCH, 29: 3791-3796, 2009). However, the benzimidazole is introduced without distinguishing normal cells and abnormal cells (i.e., cancer-expressing cells), and is known to inhibit the formation of microtubules in the same manner in normal cells and abnormal cells.

In addition, cancer cells have a property of absorbing a large amount of glucoses, which essentially uses microtubules to move a GLUT channel to a cell membrane, and in the cancer cells, it has been reported to generate about 1000 times more GLUT channels than those of the normal cells.

Accordingly, when benzimidazole derivatives are injected more intensively into cancer cells than normal cells to inhibit the formation of microtubules, the generation of the GLUT channels may be inhibited and glucose uptake may be blocked. As a result, it is known that the proliferation of cancer cells may be remarkably suppressed, whereby an in-vivo immune system attacks cancer cells whose proliferation is suppressed as described above to exhibit anti-cancer effects (see EXPERIMENTAL AND THERAPEUTIC MEDICINE 13: 595-603, 2017).

However, since the benzimidazole derivatives usually have low aqueous solubility and low bioabsorption rate, it has been reported that the benzimidazole derivatives are administered at a high concentration or in a significant amount to effectively inhibit the proliferation of cancer cells, and as a result, have significant side effects even in normal cells (see Vojnosanit Pregl. 2008 July; 65 (7):539-44, Infect Chemother 2018; 50(1):1-10).

Therefore, the benzimidazole derivatives are administered together with drugs (e.g., an H2 receptor blocker such as cimetidine or a gastric acid secretion inhibitor) that can improve absorption in the gastrointestinal tract, or it has been proposed to introduce a water-soluble substituent in order to improve the water solubility of the benzimidazole derivatives themselves.

For example, in Patent Document 1 (international Patent Publication No. WO1998/051304, published on Nov. 19, 1998), disclosed is that a 2-carbamate benzimidazole derivative inhibits the proliferation of tumors and cancers in mammals and treats viral infections, but the aqueous solubility and the bioabsorption rate are low as described above, and as a result, a pharmacological effect is not sufficient.

In Patent Document 2 (international Patent Publication No. WO2005/058870, published on Jun. 30, 2005), disclosed is that a compound, in which a substituent capable of increasing water solubility, such as a 3-hydroxypropyl group, 2,3-dihydroxypropyl group, or 2-carboxamidoethyl group is attached to a 2-amino group of a 1-aryl-2-aminobenzimidazole derivative, is used as a respiratory syncytial virus replication inhibitor, but the aqueous solubility and the bioabsorption rate are not sufficient.

In Patent Document 3 (international Patent Publication No. WO1998/056761, published on Dec. 17, 1998), there are disclosed a compound of substituting a pyranose ring derived from β-D-ribopyranose to a nitrogen atom at 1-position of a benzimidazole derivative and its use in the treatment and prevention of viral infections using the same. In Patent Document 3, the pyranose ring may contain 2 to 3 or more hydroxyl groups, so that the water solubility of the benzimidazole derivative is greatly increased, and a possibility to be used as an injection is disclosed. However, it can be seen that there is disclosed only the derivative in which the pyranose ring is linked to the 1-position of benzimidazole, and even when benzimidazole contains a 2-amino group, a reaction path that avoids the reaction to the 2-amino group is adopted.

Among these benzimidazole derivatives, 2-aminobenzimidazole derivatives, such as albendazole, fenbendazole, mebendazole, flubendazole, etc., known as anthelmintic agents, are known to exhibit surprising anti-cancer effects and thus, have newly attracted attention, but interest is also being given even to methods for improving their low water solubility and bioavailability.

Albendazole and fenbendazole, which are used as anthelmintic agents, are benzimidazole carbamate-based compounds, and are equally absorbed in cancer cells and normal cells when absorbed in cells. Therefore, it is difficult to selectively absorb these compounds only in cancer cells.

Meanwhile, in several literatures, it has been reported that glucose, as an energy source of all cells, is absorbed through a glucose transporter (GLUT) channel of the cells, but virus-infected cells use a greater amount of glucoses as an energy source than normal cells (see BMC Biology (2019) 17:59), (J Virol 89:2358-2366), (Virology. 2013; 444(1-2): 301-9).

In conclusion, it can be seen that cancer cells absorb a relatively greater amount of glucose-containing sugar compounds than normal cells.

In consideration of the above points, the phenomenon that cancer cells absorb a greater amount of sugar compound containing glucose than normal cells is utilized in a design of novel benzimidazole derivatives, and it will be intended to develop a method capable of providing these novel benzimidazole derivatives with a simple process and economical cost.

The above-described technical configuration is the background art for assisting the understanding of the present invention, and does not mean a conventional technology widely known in the art to which the present invention belongs.

SUMMARY OF THE INVENTION

An object of the present invention is to design novel benzimidazole derivatives capable of solving the above-described problems, and to provide a simple and economical method for preparing the same, and a use as an anti-cancer or antiviral agent using the same.

The objects to be solved by the present disclosure are not limited to the aforementioned object (s), and other object(s), which are not mentioned above, will be apparent to those skilled in the art from the following description.

In order to solve the above object, the present invention provides a novel benzimidazole carbamate-sugar compound conjugate compound represented by the following Chemical Formula 1.

[Chemical Formula 1]

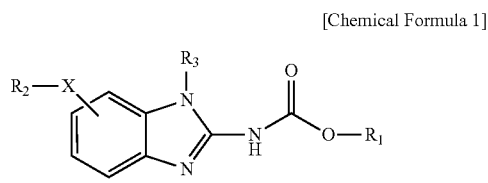

Wherein, $R_1$ is a sugar-compound residue, wherein the sugar compound is selected f rom tetrose aldose (e.g., erythrose, threose), pentose aldose (e.g., ribose, arabinose, xylose, lyxose), hexose aldose (e.g., allose, altrose, glucose, mannose, gluose, idose, galactose, talose), tetrose ketose (e.g., erythrulose), pentose ketose (e.g., ribulose, xylulose), hexose ketose (e.g., psicose, fructose, sorbose, tagatose), their isomers, oxides (CHO is converted to —COOH), deoxy derivatives (—OH is converted to —H, e.g., 2-deoxyribose, 2-deoxyglucose), amino sugars (—OH is converted to —NH, e.g., N-acetylglucosamine, N-acetylgalactosamine), and glycosides, disaccharides or polysaccharide thereof, and preferably, is selected from glucose, fructose, galactose, mannose or xylose, $R_2$ and $R_3$ are the same as or different from each other and represent hydrogen or a substituted hydrocarbon group, for example, an alkyl group having 1 to 10 carbon atoms, an aryl group or a heteroaryl group having 3 to 10 ring atoms, wherein the alkyl group, aryl group, or heteroaryl group is substituted with a substituent selected from halogen, cyano, hydroxy, thiol, amino, alkyl, alkyloxy, alkylamino, dialkylamino, aryl, aryloxy, arylamino, diarylamino or heteroaryl groups, and X is selected from the group consisting of —O—, —S—, —SO—, —SO$_2$—, —NH—, —N(R$_2$)—, —CH(R$_2$)—, and —CO—.

According to an embodiment of the present invention, the benzimidazole carbamate-sugar compound conjugate compound may be a compound represented by the following Chemical Formula 2:

[Chemical Formula 2]

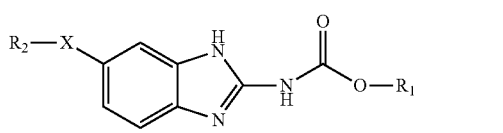

Wherein, $R_1$, $R_2$ and X are the same as those defined above.

According to an embodiment of the present invention, in Chemical Formula 1 or 2, a

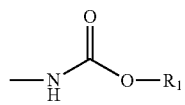

moiety may have one of the following structures:

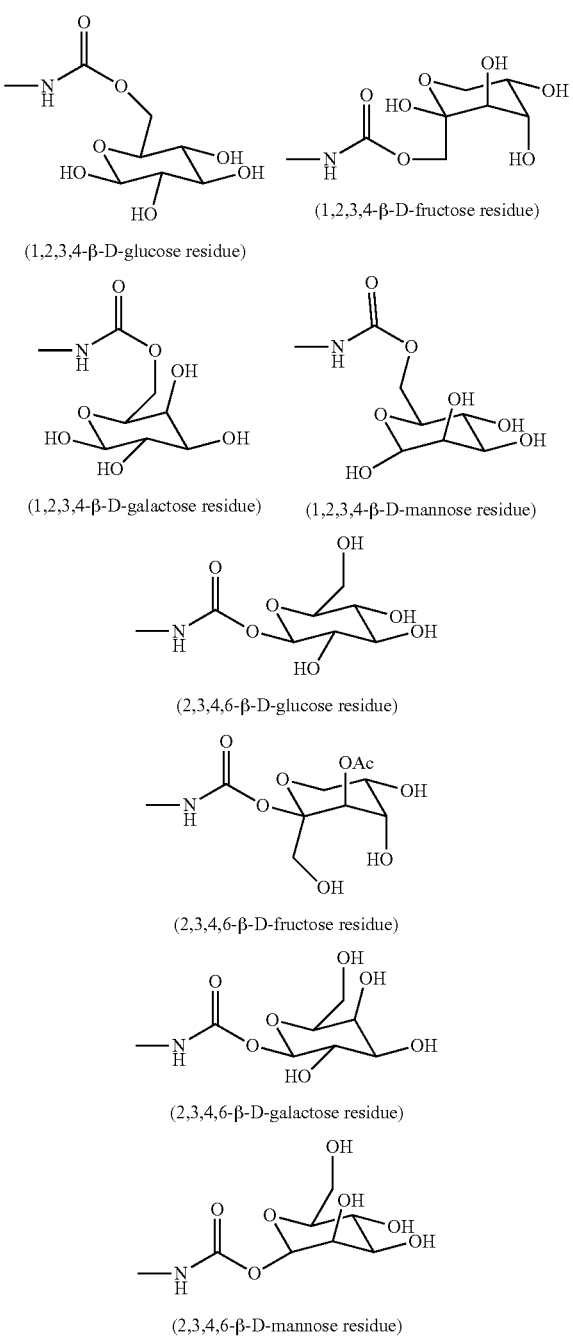

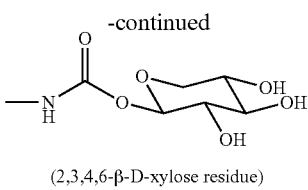

(2,3,4,6-β-D-xylose residue)

According to an embodiment of the present invention, in Chemical Formula 1 or 2, a benzimidazole moiety may have one of the following structures:

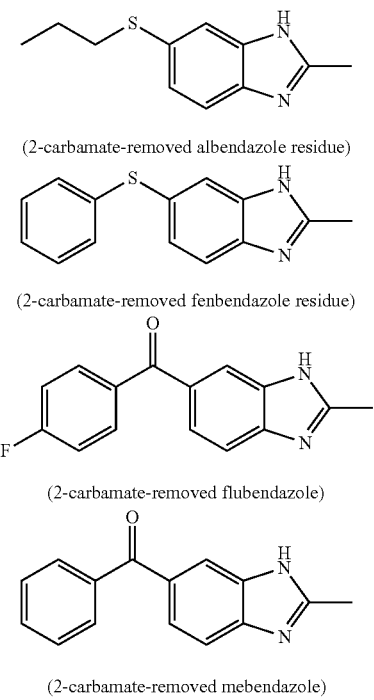

(2-carbamate-removed albendazole residue)

(2-carbamate-removed fenbendazole residue)

(2-carbamate-removed flubendazole)

(2-carbamate-removed mebendazole)

According to an embodiment of the present invention, the benzimidazole carbamate-sugar compound conjugate compound may be selected from the following compounds:

as an albendazole-J-sugar compound conjugate compound,
Albendazole-1,2,3,4-β-D-glucose,
Albendazole-1,2,3,4-β-D-fructose,
Albendazole-1,2,3,4-β-D-galactose,
Albendazole-1,2,3,4-β-D-mannose,
Albendazole-2,3,4,6-β-D-glucose,
Albendazole-2,3,4,6-β-D-fructose,
Albendazole-2,3,4,6-β-D-galactose,
Albendazole-2,3,4,6-β-D-mannose,
Albendazole-2,3,4,6-β-D-xylose;

as a fenbendazole-D-sugar compound conjugate compound,
Fenbendazole-1,2,3,4-β-D-glucose,
Fenbendazole-1,2,3,4-β-D-fructose,
Fenbendazole-1,2,3,4-β-D-galactose,
Fenbendazole-1,2,3,4-β-D-mannose,
Fenbendazole-2,3,4,6-β-D-glucose,
Fenbendazole-2,3,4,6-β-D-fructose,
Fenbendazole-2,3,4,6-β-D-galactose,
Fenbendazole-2,3,4,6-β-D-mannose,
Fenbendazole-2,3,4,6-β-D-xylose;

as a flubendazole-D-sugar compound conjugate compound,
Flubendazole-1,2,3,4-β-D-glucose,
Flubendazole-1,2,3,4-β-D-fructose,
Flubendazole-1,2,3,4-β-D-galactose,
Flubendazole-1,2,3,4-β-D-mannose,
Flubendazole-2,3,4,6-β-D-glucose,
Flubendazole-2,3,4,6-β-D-fructose,
Flubendazole-2,3,4,6-β-D-galactose,
Flubendazole-2,3,4,6-β-D-mannose,
Flubendazole-2,3,4,6-β-D-xylose; and as a mebendazole-D-sugar compound conjugate compound,
Mebendazole-1,2,3,4-β-D-glucose,
Mebendazole-1,2,3,4-β-D-fructose,
Mebendazole-1,2,3,4-β-D-galactose,
Mebendazole-1,2,3,4-β-D-mannose,
Mebendazole-2,3,4,6-β-D-glucose,
Mebendazole-2,3,4,6-β-D-fructose,
Mebendazole-2,3,4,6-β-D-galactose,
Mebendazole-2,3,4,6-β-D-mannose,
Mebendazole-2,3,4,6-β-D-xylose.

In addition, in order to solve the object, the present invention provides a preparation method of a benzimidazole carbamate-sugar compound conjugate compound represented by the following Chemical Formula 1, which is characterized by reacting and binding a primary alcohol group (—OH) of a sugar compound to a benzimidazole carbamate compound of the following Chemical Formula 1a:

[Chemical Formula 1]

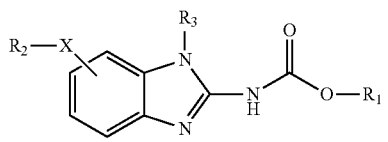

[Chemical Formula 1a]

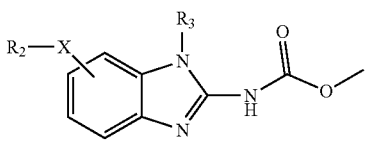

Wherein, $R_1$, $R_2$, $R_3$ and X are the same as those defined above.

In addition, in order to solve the object, the present invention provides a pharmaceutical composition capable of exhibiting anti-cancer activity by containing the benzimidazole carbamate-sugar compound conjugate compound of Chemical Formula 1 above.

According to an embodiment of the present invention, the benzimidazole carbamate-sugar compound conjugate compound of Chemical Formula 1 may be absorbed through a glucose transporter (GLUT) channel.

According to an embodiment of the present invention, the benzimidazole carbamate-sugar compound conjugate compound of Chemical Formula 1 may inhibit the formation of microtubules and inhibit the absorption of sugar compounds.

According to the present invention, it is possible to provide a novel benzimidazole carbamate-sugar compound conjugate compound having anti-cancer activity and a preparation method thereof.

It should be understood that the effects of the present invention are not limited to the effects, but include all effects that can be deduced from the detailed description of the present invention or configurations of the present invention described in appended claims.

BRIEF DESCRIPTION OF THE DRAWINGS

The above and other aspects, features and other advantages of the present invention will be more clearly understood from the following detailed description taken in conjunction with the accompanying drawings, in which:

FIG. 3 illustrates NMR spectra for albendazole-1,2,3,4-β-D-sugar compound conjugates (wherein, sugar compounds are glucose, fructose, galactose, and mannose from the top);

FIG. 4 illustrates NMR spectra for albendazole-2,3,4,6-β-D-sugar compound conjugates (wherein, sugar compounds are glucose, fructose, galactose, mannose, and xylose from the top);

FIG. 5 illustrates NMR spectra for fenbendazole-1,2,3,4-β-D-sugar compound conjugates (wherein, sugar compounds are glucose, fructose, galactose, and mannose from the top); and FIG. 6 illustrates NMR spectra for fenbendazole-2,3,4,6-β-D-sugar compound conjugates (wherein, sugar compounds are glucose, fructose, galactose, mannose, and xylose from the top).

DETAILED DESCRIPTION OF THE PREFERRED EMBODIMENT

Figure 1:
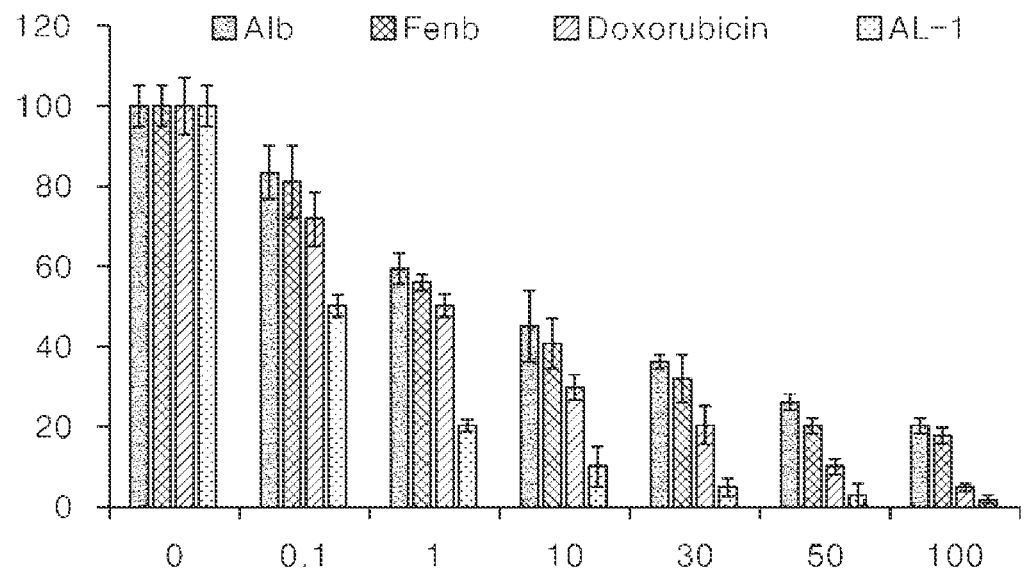
FIG. 1 is a graph showing a result of a growth inhibition test in cancer cell lines according to an embodiment of the present invention.

Before describing the present invention in detail, terms or words used in this specification should not be construed as unconditionally limited to a conventional or dictionary meaning, and the inventors of the present invention can appropriately define and use the concept of various terms in order to describe their invention in the best method. Furthermore, it should be understood that these terms or words should be interpreted as meanings and concepts consistent with the technical idea of the present invention.

That is, the terms used in this specification are only used to describe a preferred embodiment of the present invention, and are not intended to specifically limit the contents of the present invention, and it should be noted that these terms are terms defined in consideration with various possibilities of the present invention.

In addition, in this specification, it should be understood that the singular expression may include a plural expression unless clearly indicated in another meaning in the context, and even if similarly expressed in the plural, the singular expression may include the meaning of the singular number.

Throughout this specification, when a component is described as "including" another component, the component does not exclude any another component, but further includes any another component unless otherwise indicated.

Further, hereinafter, in the following description of the present invention, a detailed description of a configuration determined to unnecessarily obscure the subject matter of the present invention, for example, a known technology including the prior art may be omitted.

First, terms used in this specification are briefly defined as follows for understanding of the present invention. However, the present invention is not limited by these meanings or definitions of terms.

The term "anti-cancer agent" refers to a substance or a drug that inhibits the growth or proliferation of cancer cells.

The term "sugar compound" is used as a generic term for organic compounds consisting of sugars.

The term "tubulin" refers to a protein constituting microtubules present in almost all cells of an organism.

The term "microtubule" is made of a polymer of a protein called tubulin, and refers to an organelle that maintains a cytoskeleton and is involved in cellular motility and intracellular transport.

The term "cell division" refers to a phenomenon in which a parent cell of an organism is divided into two cells through nuclear division and cytokinesis.

Hereinafter, the present invention will be described in more detail.

Benzimidazole Carbamate-Sugar Compound Conjugate Compound

A first object of the present invention is to provide a benzimidazole carbamate-sugar compound conjugate compound represented by the following Chemical Formula 1:

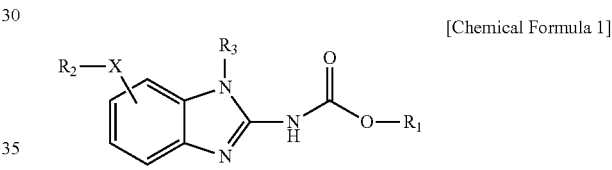

[Chemical Formula 1]

Wherein, $R_1$ is a sugar-compound residue, wherein the sugar compound is selected from tetrose aldose (e.g., erythrose, threose), pentose aldose (e.g., ribose, arabinose, xylose, lyxose), hexose aldose (e.g., allose, altrose, glucose, mannose, gluose, idose, galactose, talose), tetrose ketose (e.g., erythrulose), pentose ketose (e.g., ribulose, xylulose), hexose ketose (e.g., psicose, fructose, sorbose, tagatose), their isomers, oxides (CHO is converted to —COOH), deoxy derivatives (—OH is converted to —H, e.g., 2-deoxyribose, 2-deoxyglucose), amino sugars (—OH is converted to —NH, e.g., N-acetylglucosamine, N-acetylgalactosamine), and glycosides, disaccharides or polysaccharide thereof, and preferably, is selected from glucose, fructose, galactose, mannose or xylose, $R_2$ and $R_3$ are the same as or different from each other and represent hydrogen or a substituted hydrocarbon group, for example, an alkyl group having 1 to 10 carbon atoms, an aryl group or a heteroaryl group having 3 to 10 ring atoms, wherein the alkyl group, aryl group, or heteroaryl group is substituted with a substituent selected from halogen, cyano, hydroxy, thiol, amino, alkyl, alkyloxy, alkylamino, dialkylamino, aryl, aryloxy, arylamino, diarylamino or heteroaryl groups, and X is selected from the group consisting of —O—, —S—, —SO—, —SO$_2$—, —NH—, —N($R_2$)—, —CH$_2$—, —CH($R_2$)—, and —CO—.

The compound of Chemical Formula 1 may be understood as a form in which a sugar compound residue is bound to benzimidazole carbamate.

According to an embodiment of the present invention, the benzimidazole carbamate-sugar compound conjugate compound may be a compound represented by the following Chemical Formula 2:

[Chemical Formula 2]

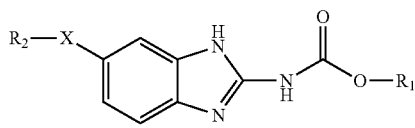

Wherein, $R_1$, $R_2$ and X are the same as those defined above.

According to an embodiment of the present invention, in Chemical Formula 1 or 2, a

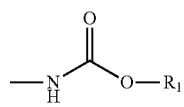

moiety may have one of the following structures:

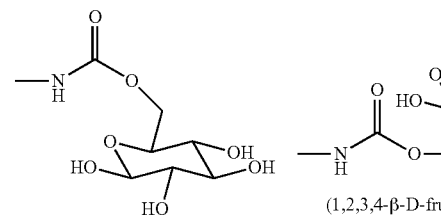
(1,2,3,4-β-D-glucose residue)    (1,2,3,4-β-D-fructose residue)

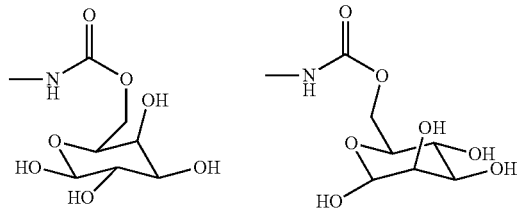
(1,2,3,4-β-D-galactose residue)    (1,2,3,4-β-D-mannose residue)

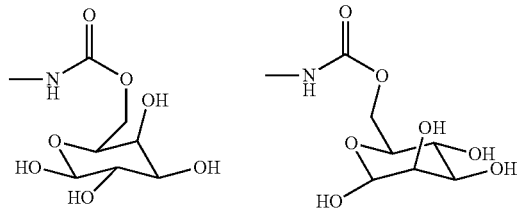
(2,3,4,6-β-D-glucose residue)

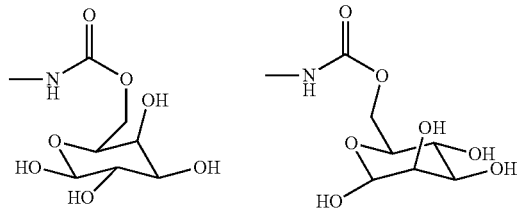
(2,3,4,6-β-D-fructose residue)

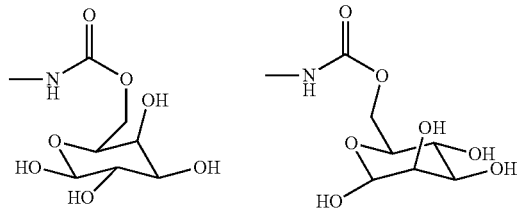
(2,3,4,6-β-D-galactose residue)

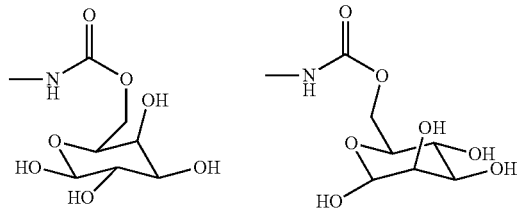
(2,3,4,6-β-D-mannose residue)

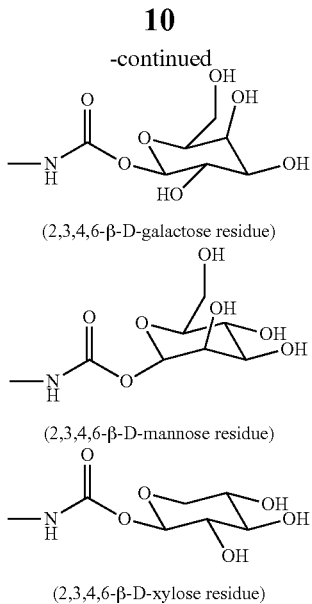
(2,3,4,6-β-D-xylose residue)

According to an embodiment of the present invention, in Chemical Formula 1 or 2, a benzimidazole moiety may have one of the following structures:

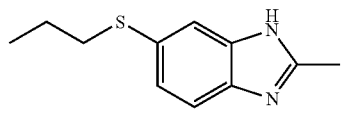
(2-carbamate-removed albendazole residue)

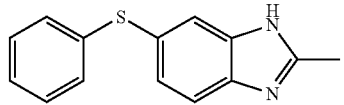
(2-carbamate-removed fenbendazole residue)

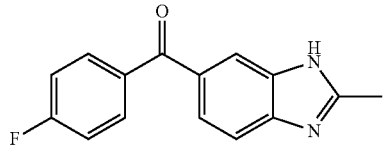
(2-carbamate-removed flubendazole)

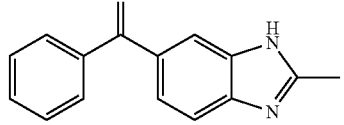
(2-carbamate-removed mebendazole)

According to an embodiment of the present invention, the benzimidazole carbamate-sugar compound conjugate compound may be selected from the following compounds:
as an albendazole-D-sugar compound conjugate compound,
Albendazole-1,2,3,4-β-D-glucose,
Albendazole-1,2,3,4-β-D-fructose,
Albendazole-1,2,3,4-β-D-galactose,
Albendazole-1,2,3,4-β-D-mannose,
Albendazole-2,3,4,6-β-D-glucose,
Albendazole-2,3,4,6-β-D-fructose,
Albendazole-2,3,4,6-β-D-galactose,
Albendazole-2,3,4,6-β-D-mannose, Albendazole-2,3,4,6-β-D-xylose;
as a fenbendazole-D-sugar compound conjugate compound,
Fenbendazole-1,2,3,4-β-D-glucose,
Fenbendazole-1,2,3,4-β-D-fructose,
Fenbendazole-1,2,3,4-β-D-galactose,
Fenbendazole-1,2,3,4-β-D-mannose,
Fenbendazole-2,3,4,6-β-D-glucose,
Fenbendazole-2,3,4,6-β-D-fructose,
Fenbendazole-2,3,4,6-β-D-galactose,
Fenbendazole-2,3,4,6-β-D-mannose,
Fenbendazole-2,3,4,6-β-D-xylose;
as a flubendazole-D-sugar compound conjugate compound,
Flubendazole-1,2,3,4-β-D-glucose,
Flubendazole-1,2,3,4-β-D-fructose,
Flubendazole-1,2,3,4-β-D-galactose,
Flubendazole-1,2,3,4β-D-mannose,
Flubendazole-2,3,4,6-β-D-glucose,
Flubendazole-2,3,4,6-β-D-fructose,
Flubendazole-2,3,4,6-β-D-galactose,
Flubendazole-2,3,4,6-β-D-mannose,
Flubendazole-2,3,4,6-β-D-xylose; and
as a mebendazole-D-sugar compound conjugate compound,
Mebendazole-1,2,3,4-β-D-glucose,
Mebendazole-1,2,3,4-β-D-fructose,
Mebendazole-1,2,3,4-β-D-galactose,
Mebendazole-1,2,3,4-β-D-mannose,
Mebendazole-2,3,4,6-β-D-glucose,
Mebendazole-2,3,4,6-β-D-fructose,
Mebendazole-2,3,4,6-β-D-galactose,
Mebendazole-2,3,4,6-β-D-mannose,
Mebendazole-2,3,4,6-β-LD-xylose.

Preparation Method of Benzimidazole Carbamate-Sugar Compound Conjugate Compound

A second object of the present invention is to provide a preparation method of a benzimidazole carbamate-sugar compound conjugate compound represented by the following Chemical Formula 1, by reacting and binding a primary alcohol group (—OH) of a sugar compound to a benzimidazole carbamate compound of the following Chemical Formula 1a:

[Chemical Formula 1]

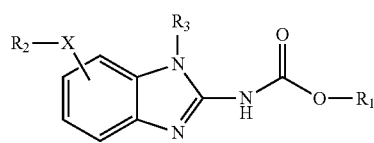

[Chemical Formula 1a]

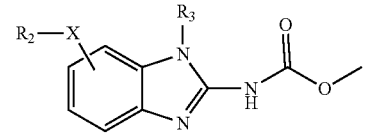

Wherein, $R_1$, $R_2$, $R_3$ and X are the same as those defined above.

The benzimidazole carbamate-sugar compound conjugate compound according to the present invention may be prepared by various methods, and an example of the preparation method is provided below.

As an example of preparing the benzimidazole carbamate-sugar compound conjugate compound according to the present invention, the following Reaction Schemes 1 to 3 may be presented.

Reaction Scheme 1 shows a reaction of preparing glucose pentaacetate (1,2,3,4,6-Penta-O-acetyl-β-D-glucopyranose) which is an intermediate used for preparing the benzimidazole carbamate-sugar compound according to the present invention from D-glucose and preparing 1,2,3,4-Tetra-o-acetyl-β-D-glucopyranose or 2,3,4,6-Tetra-o-acetyl-β-D-glucopyranose from glucose pentaacetate (1,2,3,4,6-Penta-O-acetyl-β-D-glucopyranose).

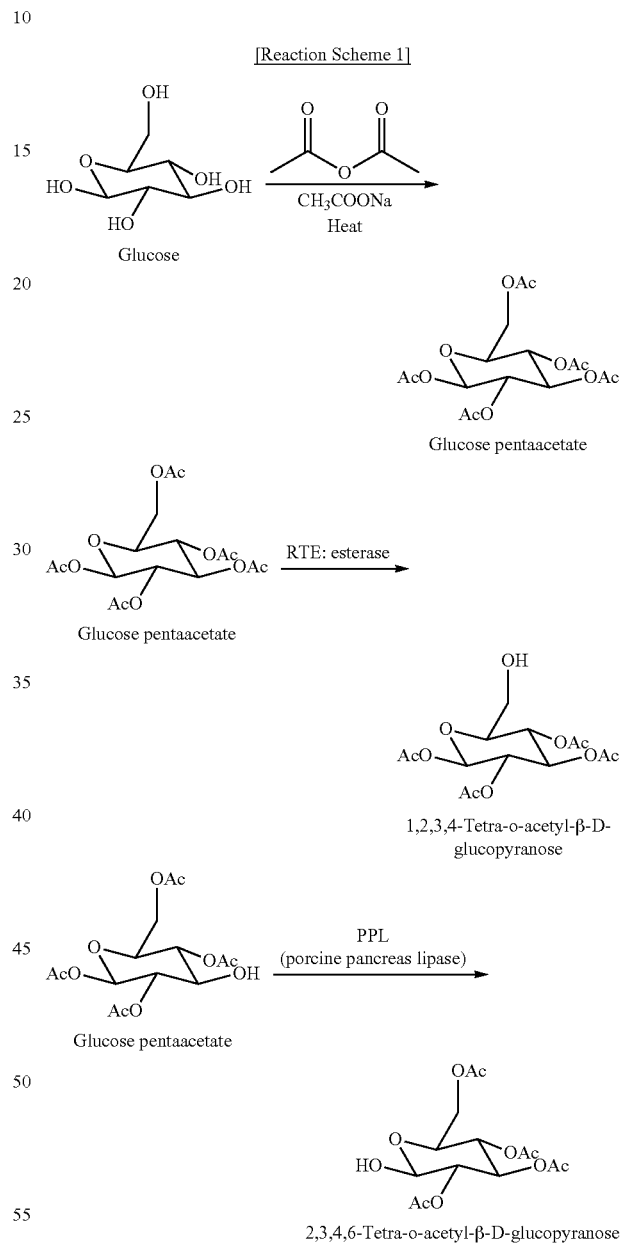

Reaction Scheme 2 shows a reaction for preparing albendazole-1,2,3,4-Tetra-o-acetyl-β-D-glucose, which is the benzimidazole carbamate-sugar compound conjugate compound according to an embodiment of the present invention. The albendazole-1,2,3,4-Tetra-o-acetyl-β-D-glucose is a form in which a primary alcohol moiety of glucose (1,2,3,4-Tetra-o-acetyl-β-D-glucopyranose) is reacted and bound with albendazole, which is representative benzimidazole carbamate.

[Reaction Scheme 2]

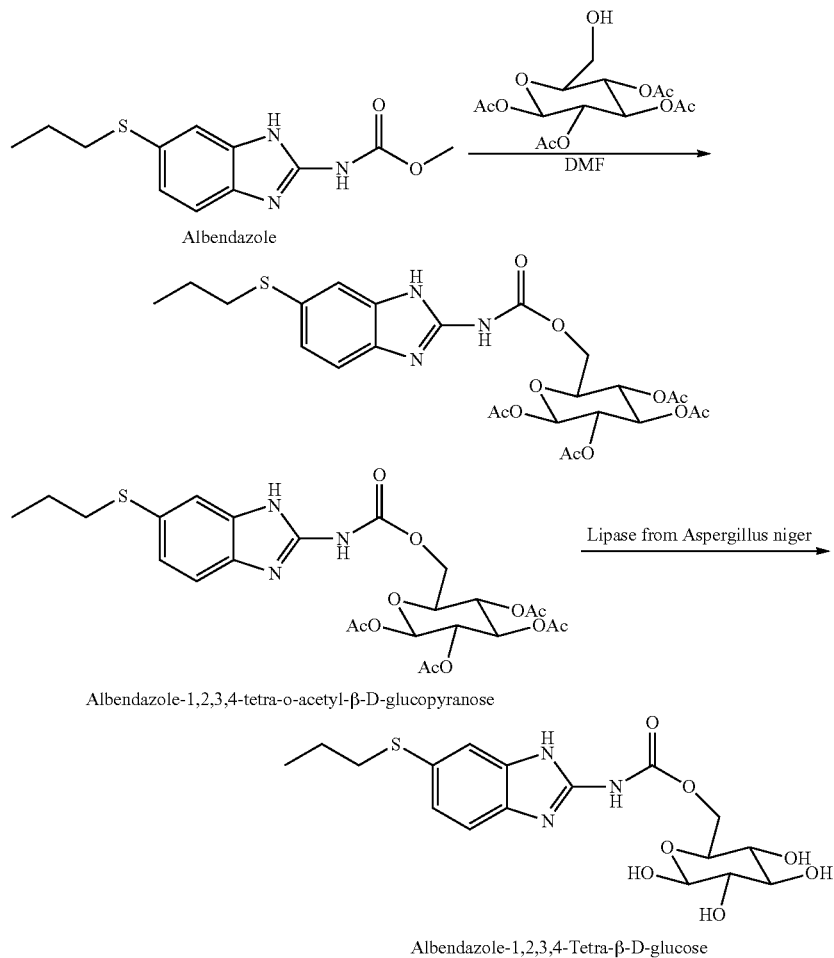

Reaction Scheme 3 shows a reaction for preparing albendazole-2,3,4,6-tetra-o-acetyl-β-D-glucose, which is the benzimidazole carbamate-sugar compound conjugate compound according to an embodiment of the present invention. The albendazole-2,3,4,6-tetra-o-acetyl-β-D-glucose is a form in which a primary alcohol moiety of glucose (2,3,4,6-Tetra-o-acetyl-β-D-glucopyranose) is reacted and bound with albendazole, which is representative benzimidazole carbamate.

[Reaction Scheme 3]

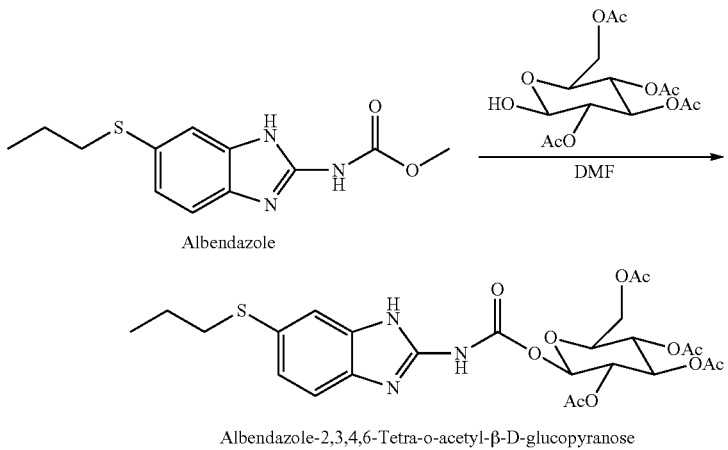

-continued

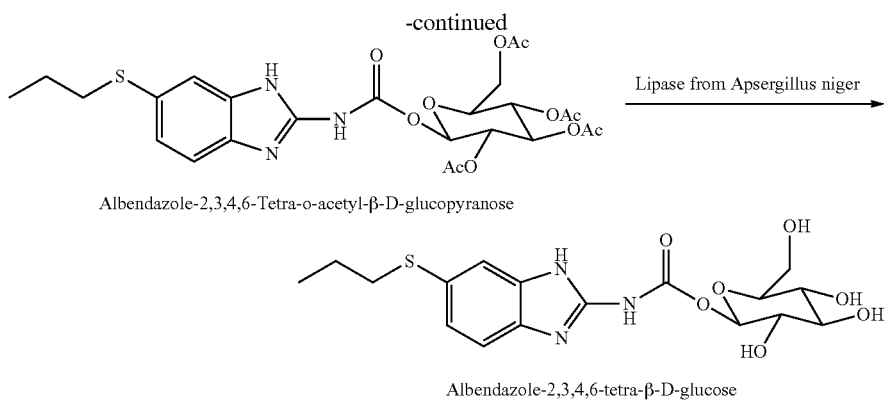

Albendazole-2,3,4,6-Tetra-o-acetyl-β-D-glucopyranose

Albendazole-2,3,4,6-tetra-β-D-glucose

The benzimidazole carbamate-sugar compound conjugate compound obtained in Reaction Schemes 1 to 3 may be isolated and/or purified by a conventional method, and then confirmed by a spectroscopic method (e.g., 1H-NMR) and the like.

Use as Anti-Cancer Agent of Benzimidazole Carbamate-Sugar Compound Conjugate Compound A third object of the present invention is to provide a pharmaceutical composition or a pharmacological composition containing the benzimidazole carbamate-sugar compound conjugate compound of Chemical Formula 1 above.

According to an embodiment of the present invention, there is provided a pharmaceutical composition having anti-cancer activity by containing the benzimidazole carbamate-sugar compound conjugate compound of Chemical Formula 1.

According to an embodiment of the present invention, there is provided a pharmaceutical composition in which the benzimidazole carbamate-sugar compound conjugate compound of Chemical Formula 1 is absorbed through a glucose transporter (GLUT) channel.

The benzimidazole carbamate-sugar compound conjugate compound of Chemical Formula 1 according to an embodiment of the present invention is characterized to selectively exhibit an anti-cancer effect by targeting only cancer cells.

One of the features of the present invention is that when the albendazole-glucose compound or fenbendazole-glucose compound according to an embodiment of the present invention is absorbed into cells in a form in which glucose is bound to albendazole or fenbendazole, the albendazole-glucose compound or fenbendazole-glucose compound is designed to be absorbed through a glucose transporter (GLUT) channel by glucose bound to the compound. It is known that the GLUT channel is more activated in cancer cells or virus-infected cells than in normal cells. In particular, it is reported that cancer cells form about 1000 times more GLUT channels than normal cells. The benzimidazole carbamate-sugar compound conjugate compound according to the present invention is expected to be absorbed intensively in cancer cells with more activated GLUT channels than in normal cells (L. Quan et al./Journal of Molecular Structure 1203 (2020) 127361).

According to an embodiment of the present invention, the benzimidazole carbamate-sugar compound conjugate compound of Chemical Formula 1 provides a pharmaceutical composition which inhibits the formation of microtubules and inhibits the absorption of sugar compounds.

One of advantages of the present invention is that the novel benzimidazole carbamate-sugar compound conjugate compound according to the present invention is mainly absorbed only in cancer cells rather than in normal cells, and then binds to tubulin which forms microtubules, which are known characteristics of conventional benzimidazole compound derivatives to inhibit the formation of microtubules and inhibits cell division to block the absorption of sugar compounds including glucose, which is a cellular energy source, thereby effectively inducing the death of cancer cells.

Therefore, the novel benzimidazole carbamate-sugar compound conjugate compound according to the present invention is mainly absorbed intensively in cancer cells not only to be designed to minimize toxicity to normal cells, but also to be expected to be usefully used as an anti-cancer compound for cancer treatment.

Hereinafter, the present invention will be described in more detail with reference to Examples. However, the following Examples are for explaining the present invention in more detail, and the scope of the present invention is not limited by the following Examples. The following Examples can be appropriately modified and changed by those skilled in the art within the scope of the present invention.

EXAMPLES

Example 1: Preparation of albendazole-1,2,3,4-Tetra-β-D-glucose (AL-1)

<Example 1-A> Preparation of glucose pentaacetate
(1,2,3,4,6-Penta-O-acetyl-β-D-glucopyranose)

[Reaction Formula 1]

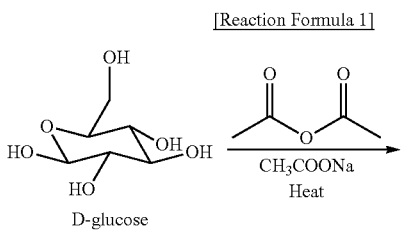

D-glucose

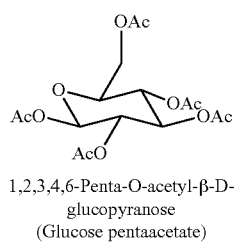

1,2,3,4,6-Penta-O-acetyl-β-D-glucopyranose
(Glucose pentaacetate)

Glucose pentaacetate was prepared from glucose according to Reaction Formula 1 above, and the reaction procedure and conditions referred to a method described in document (Ciencia e Agrotecnologia 41(2):201-208, March/April 2017).

1 g of glucose (0.0056 mol), 10 mL of acetic anhydride (0.317 mol), and 1 g of ethyl sodium (0.012 mol) were added in a flask and reacted to obtain glucose pentaacetate (1,2,3,4,6-Penta-O-acetyl-5-D-glucopyranose).

The product was analyzed by a 1H-NMR spectrum to confirm the production of glucose pentaacetate. 1H-NMR data were as follows.

H NMR dH(400 MHz; CDCl3) 5.72, (1H, d, J 8.3), 5.11-5.16 (1H, m), 5.25, (1H, t J 9.4), 5.11-5.16 (1H, m), 3.82-3.86 (1H, m), 4.29 (1H dd, J 12.4, J 4.7), 4.12 (1H, dd j 12.4, J 2.4), 2.01 (3H, s), 2.03, (3H, s), 2.09 (3H, s), 2.03 (3H, s), 2.12 (3H, s)

<Example 1-B> Preparation of 1,2,3,4-Tetra-o-acetyl-β-D-glucopyranose

[Reaction Formula 2]

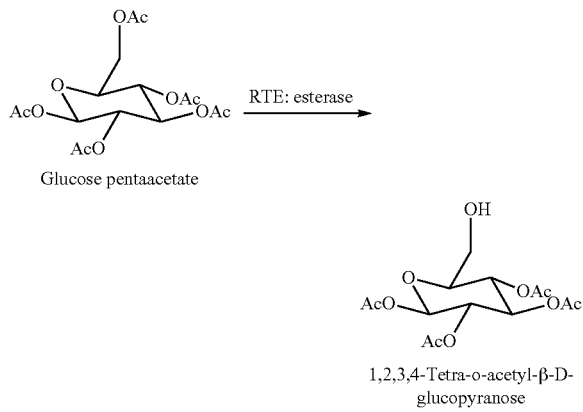

1,2,3,4-Tetra-o-acetyl-β-D-glucopyranose was synthesized from glucose pentaacetate according to Reaction Formula 2 above, and the reaction procedure and conditions referred to a method described in document (J. Chem. Soc., Perkin Trans. 1, 1998).

The glucose pentaacetate (3.0 g, 7.66 mmol) prepared in Example 1-A was suspended in 350 ml of a phosphate buffer solution at 30.8° C., and then added with esterase (40 mg) and reacted to obtain 1,2,3,4-Tetra-o-acetyl-β-D-glucopyranose.

The product was analyzed by a 1H-NMR spectrum to confirm the production of 1,2,3,4-Tetra-o-acetyl-β-D-glucopyranose. 1H-NMR data were as follows.

H NMR dH(400 MHz; CDCl3) 1.97 (3H, s, CH3CO), 1.99 (3H, s, CH3CO), 2.03 (3H, s, CH3CO), 2.13 (3H, s, CH3CO), 2.37 (1H, m, OH), 3.55 (1H, m, Hb-6), 3.68 (1H, m, Ha-6), 3.89 (1H, ddd, J 2.29, 4.19 and 10, 11-5), 5.04 (1H, dd, J 3.7 and 10, 1H-2), 5.07 (1H, dd, J 9.8 and 10, H-4), 5.48 (1H, app t, J 10 and 10, H-3) and 6.3 (1H, d, J 3.7, H-1)

<Example 1-C> Preparation of albendazole-1,2,3,4-tetra-o-acetyl-β-D-glucopyranose

[Reaction Formula 3]

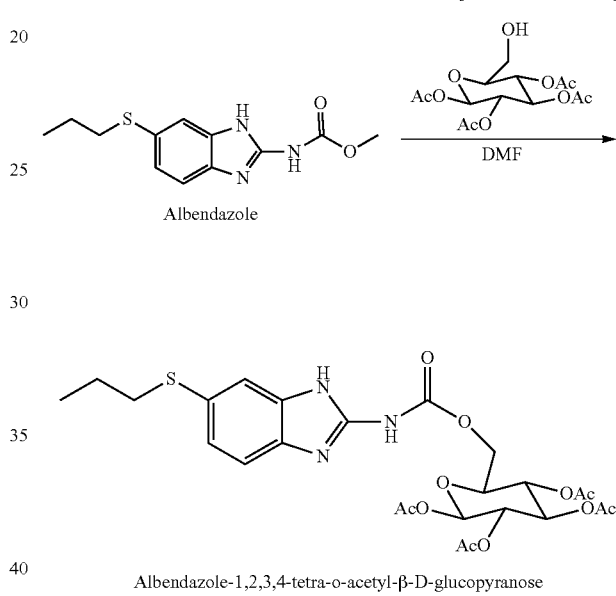

Albendazole-1,2,3,4-tetra-o-acetyl-β-D-glucopyranose

According to Reaction Formula 3 above, 1,2,3,4-Tetra-o-acetyl-β-D-glucopyranose was added to albendazole to synthesize albendazole-1,2,3,4-tetra-o-acetyl-β-D-glucopyranose.

A magnetic bar was put in a flask, and albendazole (1 g, 0.00377 mmole) and the compound, 1, 2, 3, 4-Tetra-o-acetyl-β-D-glucopyranose (13.3 g, 0.0377 mmole) obtained in Example 1-B were added and 120 ml of DMF was added thereto. After mixing at room temperature, the mixture was reacted at 90° C. for 24 hours under an acid catalyst using a magnetic stirrer. After the reaction, the reaction product cooled to room temperature was distilled under reduced pressure and purified using MeOH:EA to obtain 1.3 g of a compound, albendazole-1,2,3,4-tetra-o-acetyl-β-D-glucopyranose (yield 59%).

The product was analyzed by a 1H-NMR spectrum to confirm the production of albendazole-1,2,3,4-tetra-o-acetyl-β-D-glucopyranose. 1H-NMR data were as follows.

1H NMR (400 MHz, DMSO-d6): δ=11.62 (s, 1H), 7.42 (s, 1H), 7.32 (d, J=7.49 Hz, 1H), 7.09 (d, J=7.50 Hz, 1.46 Hz, 1H), 0.95 (t, J=7.96 Hz, 3H), 1.54 (m, 2H), 2.58 (t, J=7.14, 4.48 Hz, 2H), 5.04 (d, J=7.2 Hz, 1H), 3.99-3.90 (m, 1H), 3.80-3.71 (m, 1H), 3.62-3.32 (m, 4H)

<Example 1-D> Preparation of albendazole-1,2,3,4-tetra-β-D-glucose

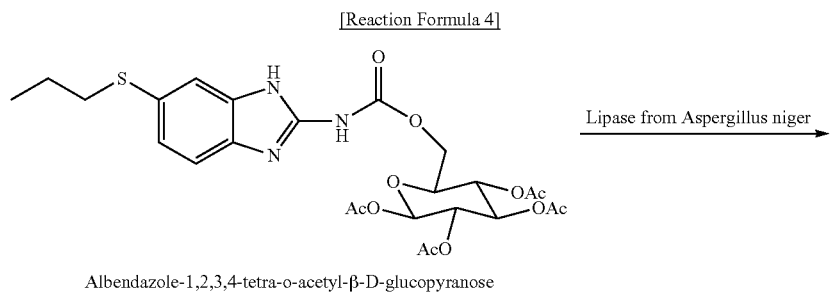

Albendazole-1,2,3,4-tetra-o-acetyl-β-D-glucopyranose

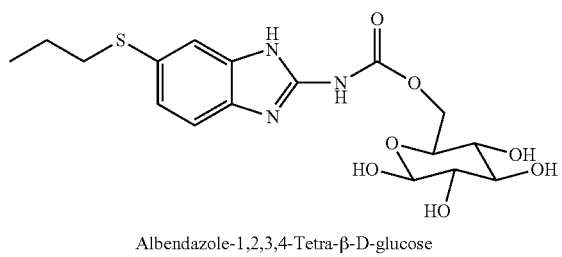

Albendazole-1,2,3,4-Tetra-β-D-glucose

According to Reaction Formula 4 above, lipase was added to albendazole-1,2,3,4-Tetra-o-acetyl-β-D-glucopyranose to synthesize albendazole-1,2,3,4-tetra-β-D-glucose.

A magnetic bar was put in a flask, the compound, albendazole-1,2,3,4-tetra-o-acetyl-β-D-glucopyranose (100 mg, 0.17 mmol) obtained in Example 1-C and 0.1 g of A-ANL powder were added, and a mixed solution of 30 ml of acetonitrile and 20 ml of 0.1M phosphate buffer was added and reacted at room temperature for 48 hours. The reaction product was extracted with methanol and ethyl acetate, and then purified by a silica column to obtain 32 mg of albendazole-1,2,3,4-Tetra-o-acetyl-?-D-glucose (yield 45%).

The product was analyzed by a 1H-NMR spectrum to confirm the production of albendazole-1,2,3,4-Tetra-o-acetyl-β-D-glucose. 1H-NMR data were as follows.

1H NMR (400 MHz, DMSO-d6): δ=11.62 (s, 1H), 7.42 (s, 1H), 7.32 (d, J=7.49 Hz, 1H), 7.09 (d, J=7.50 Hz, 1.46 Hz, 1H), 0.95 (t, J=7.96 Hz, 3H), 1.54 (m, 2H), 2.58 (t, J=7.14, 4.48 Hz, 2H), 5.04 (d, J=7.2 Hz, 1H), 3.99-3.90 (m, 1H), 3.80-3.71 (m, 1H), 3.62-3.32 (m, 4H)

Example 2: Preparation of albendazole-2,3,4,6-Tetra-o-acetyl-p-D-glucose

<Example 2-A> Preparation of glucose pentaacetate (1,2,3,4,6-Penta-O-acetyl-β-D-glucopyranose)

Glucose pentaacetate (1,2,3,4,6-Penta-O-acetyl-5-D-glucopyranose) was prepared in the same manner as in Example 1-A.

<Example 2-B> Preparation of 2,3,4,6-Tetra-o-acetyl-β-D-glucopyranose

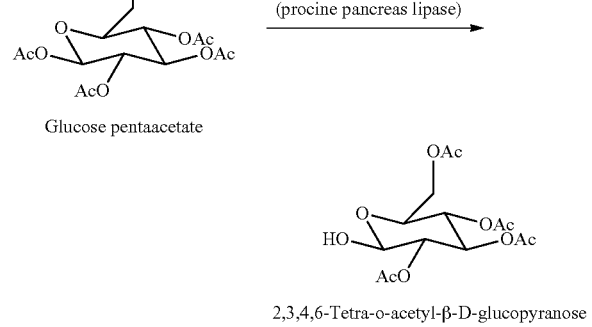

2,3,4,6-Tetra-o-acetyl-β-D-glucopyranose was synthesized from glucose pentaacetate according to Reaction Formula 5 above, and the reaction procedure and conditions referred to a method described in document (J. Org. Chem., 1988, 53, 4939-4945).

Glucose (10 mg/mL, PBS) was suspended in a 10% (v/v) DMF/PBS buffer (0.05 M, pH 7). Lipase (0.75 g/mmol of sugar) was added and reacted to obtain 2,3,4,6-Tetra-o-acetyl-β-D-glucopyranose.

The product was analyzed by a 1H-NMR spectrum to confirm the production of 2,3,4,6-Tetra-o-acetyl-β-D-glucopyranose. 1H-NMR data were as follows.

H NMR (CDC1) 6 5.51 (t, 1H, H2, J=9.8 Hz), 5.43 (d, 1H, Hla, J=3.5 Hz), 5.22 (t, 1H, H30, J=9.4 Hz), 5.05 (dt, 2H,

H44), 4.92-4.82 (m, 2H, 4.72 (d, 1H, HlP, J=4.7 Hz), 4.28-3.98 (m, 5H), 3.77-3.47 (m, 1H, H5P), 2.06 (s, 3H, acetyl), 2.05 (s, 3H, acetyl), 2.01 (9, 3H, acetyl), 2.00 (s, 3H, acetyl), 1.99 (s, 3H, acetyl)

<Example 2-C> Preparation of albendazole-2,3,4,6-tetra-o-acetyl-β-D-glucopyranose

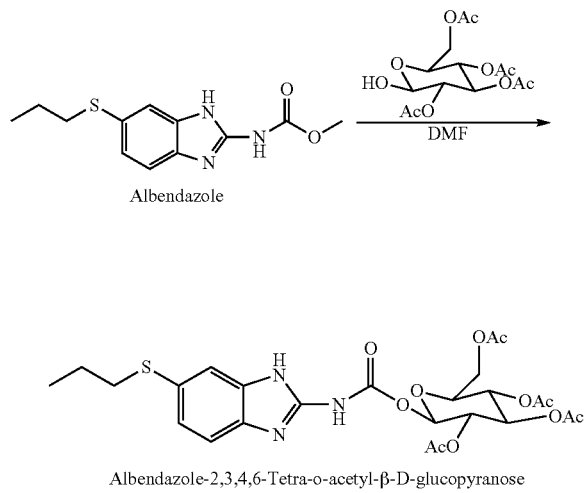

According to Reaction Formula 6 above, 2,3,4,6-Tetra-o-acetyl-r-D-glucopyranose was added to albendazole to synthesize albendazole-2,3,4,6-tetra-o-acetyl-S-D-glucopyranose.

A magnetic bar was put in a flask, and albendazole (1 g, 0.00377 mmole) and the compound, 2,3,4,6-Tetra-o-acetyl-β-D-glucopyranose (13.3 g, 0.0377 mmole) obtained in Example 2-B were added and 120 ml of DMF was added thereto. After mixing at room temperature, the mixture was reacted at 90° C. for 24 hours using a magnetic stirrer. After the reaction, the reaction product cooled to room temperature was distilled under reduced pressure and purified using MeOH:EA to obtain 1.2 g of a compound, albendazole-2,3,4,6-tetra-o-acetyl-f-D-glucopyranose (yield 52%).

The product was analyzed by a 1H-NMR spectrum to confirm the production of albendazole-2,3,4,6-tetra-o-acetyl-β-D-glucopyranose. 1H-NMR data were as follows.

1H NMR (400 MHz, DMSO-d6): δ=11.62 (s, 1H), 7.42 (s, 1H) 7.32 (d, J=7.49 Hz, 1H), 7.09 (d, J=7.50 Hz, 1.46 Hz, 1H), 0.95 (t, J=7.96 Hz, 3H), 1.54 (m, 2H), 2.58 (t, J=7.14, 4.48 Hz, 2H), 5.04 (d, J=7.2 Hz, 1H), 3.99-3.90 (m, 1H), 3.80-3.71 (m, 1H), 3.62-3.32 (m, 4H)

<Example 2-D> Preparation of albendazole-2,3,4,6-tetra-β-D-glucose

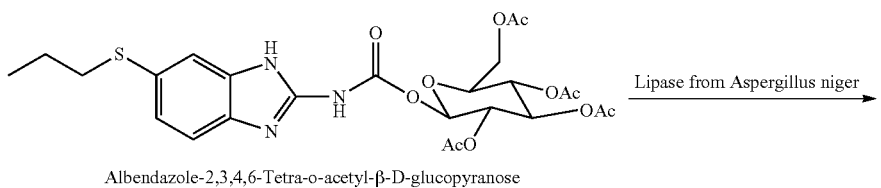

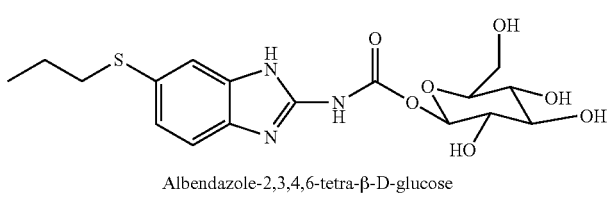

Albendazole-2,3,4,6-tetra-β-D-glucose

According to Reaction Formula 7 above, lipase was added to albendazole-2,3,4,6-Tetra-o-acetyl-β-D-glucopyranose to synthesize albendazole-2,3,4,6-tetra-β-D-glucose.

A magnetic bar was put in a flask, the compound, albendazole-2,3,4,6-tetra-o-acetyl-β-D-glucopyranose (100 mg, 0.17 mmol) obtained in Example 2-C and 0.1 g of A-ANL powder were added, and a mixed solution of 30 ml of acetonitrile and 20 ml of 0.1M phosphate buffer was added and reacted at room temperature for 48 hours. The reaction product was extracted with methanol and ethyl acetate, and then purified by a silica column to obtain 30 mg of albendazole-2,3,4,6-Tetra-o-acetyl-β-D-glucose (yield 42.1%).

The product was analyzed by a 1H-NMR spectrum to confirm the production of albendazole-1,2,3,4-Tetra-o-acetyl-β-D-glucose. 111-NMR data were as follows. 1H NMR (400 MHz, DMSO-d6) δ=11.62 (s, 1H), 7.42 (s, 1H) 7.32 (d, J=7.49 Hz, 1H), 7.09 (d, J=7.50 Hz, 1.46 Hz, 1H), 0.95 (t, J=7.96 Hz, 3H), 1.54 (m, 2H), 2.58 (t, J=7.14, 4.48 Hz, 2H), 5.04 (d, J=7.2 Hz, 1H), 3.99-3.90 (m, 1H), 3.80-3.71 (m, 1H), 3.62-3.32 (m, 4H)

Example 3: Preparation of albendazole-1,2,3,4-Tetra-β-D-fructose (AL-2)

Albendazole-1, 2, 3, 4-Tetra-β-D-fructose (AL-2) was prepared in the same manner as in Example 1, except for using fructose instead of glucose.

Example 4: Preparation of Fenbendazole-1,2,3,4-Tetra-β-D-glucose (FB-1)

Fenbendazole-1,2,3,4-Tetra-β-D-glucose (FB-1) was prepared in the same manner as in Example 1, except for using fenbendazole instead of albendazole.

Example 5: Preparation of Fenbendazole-1,2,3,4-Tetra-β-D-fructose (FB-2)

Fenbendazole-1,2,3,4-Tetra-β-D-fructose (FB-2) was prepared in the same manner as in Example 1, except for using fenbendazole instead of albendazole and using fructose instead of glucose.

Test Example 1: Cancer Cell Line Growth Inhibition Test

A human lung cancer cell line A549, a cervical cancer cell line Hela, and a colorectal cancer cell line HT-29 were adopted from the Korea Cell Line Bank (KCLB, Seoul, Korea) and cultured in a culture medium.

In a humidified cell culture incubator containing 5% $CO_2$ at 37° C. using a DMEM and a 10% culture flask, fetal bovine serum (FBS), 0.1 mM MEM non-essential amino acid (NEAA), 2 mM L-glutamine, and 1% penicillin-streptomycin were trypsinized every 2 to 3 days according to the instructions provided by the KCLB to subculture the cells. The culture was cultured until reached 80% to 90% of confluence, and the cells were successively transferred to a culture flask for a cancer cell line growth inhibition test.

A cancer cell line, a human lung cancer cell line A549, a cervical cancer cell line Hela, and a colorectal cancer cell line HT-29 to be tested were seeded in a 96-well plate at about 10,000 cells per well. After 24 hours, as shown in Table 1 below, 4 types of compounds were added to each well at 7 concentrations and incubated for 72 hours.

| Compound | Concentration |
|---|---|
| Albendazole | 0 μM, 0.1 μM, 1 μM, 10 μM, 30 μM, 50 μM, 100 μM |
| Fenbendazole | 0 μM, 0.1 μM, 1 μM, 10 μM, 30 μM, 50 μM, 100 μM |
| Doxorubicin | 0 μM, 0.1 μM, 1 μM, 10 μM, 30 μM, 50 μM, 100 μM |
| Albendazole-sugar compound (albendazole-glucose) | 0 μM, 0.1 μM, 1 μM, 10 μM, 30 μM, 50 μM, 100 μM |

In Table 1 above, the albendazole, fenbendazole and doxorubicin were commercially available compounds, and the albendazole-sugar compound was prepared in Example 1-D.

After incubation, the medium was removed and the cell viability in each well was measured using a WST-8 cell viability assay kit (Quanti-Max™, BIOMAX) and according to a procedure instructed by a manufacturer.

The analysis used a principle that dehydrogenase of living cells decomposed tetrazolium salt to generate formazan, and through this, the living cells were quantitatively evaluated.

Reduced formazan salt was soluble in a cell culture medium and an amount of formazan was directly proportional to the number of living cells (Slater, T. et al. (1963) Biochem. Biophys. Acta 77:383. van de Loosdrecht, A. A., et al. J. Immunol. Methods 174: 311-320, 1994. Alley, M. C., et al. Cancer Res. 48: 589-601, 1988.).

FIG. 1 illustrates the result of the cancer cell line growth inhibition test. As can be seen in FIG. 1, it can be seen that the albendazole-sugar compound (AL-1) has the most excellent cancer cell line growth inhibition efficiency.

Test Example 2: Toxicity Test in Normal Cell Line

A normal lung cell line MRC-5 and a normal colon CCD-18Co cell line were adopted from the Korea Cell Line Bank (KCLB) (Seoul, Korea) and cultured in a complete culture medium.

In a humidified cell culture incubator containing 5% $Co_2$ at 37° C. using a DMEM and a 10% culture flask, fetal bovine serum (FBS), 0.1 mM MEM non-essential amino acid (NEAA), 2 mM L-glutamine, and 1% penicillin-streptomycin were trypsinized every 2 to 3 days according to the instructions provided by the KCLB to subculture the cells. The culture was cultured until reached 80% to 90% of confluence, and the cells were successively transferred to a culture flask for a cancer cell line growth inhibition test.

The normal cell lines MRC-5 and CCD-18Co were seeded in a 96-well plate at about 10000 cells per well. After 24 hours, as shown in Table 2 below, 4 types of compounds were added to each well at 6 concentrations and incubated for 72 hours.

TABLE 2

| Compound | Concentration |
|---|---|
| Albendazole | 0 μM, 1 μM, 10 μM, 30 μM, 50 μM, 100 μM |
| Fenbendazole | 0 μM, 1 μM, 10 μM, 30 μM, 50 μM, 100 μM |
| Doxorubicin | 0 μM, 1 μM, 10 μM, 30 μM, 50 μM, 100 μM |
| Albendazole-sugar compound (albendazole-glucose) | 0 μM, 1 μM, 10 μM, 30 μM, 50 μM, 100 μM |

In the same manner as in Test Example 1, the cell viability and analysis were performed in the normal cell lines.

Figure 2:
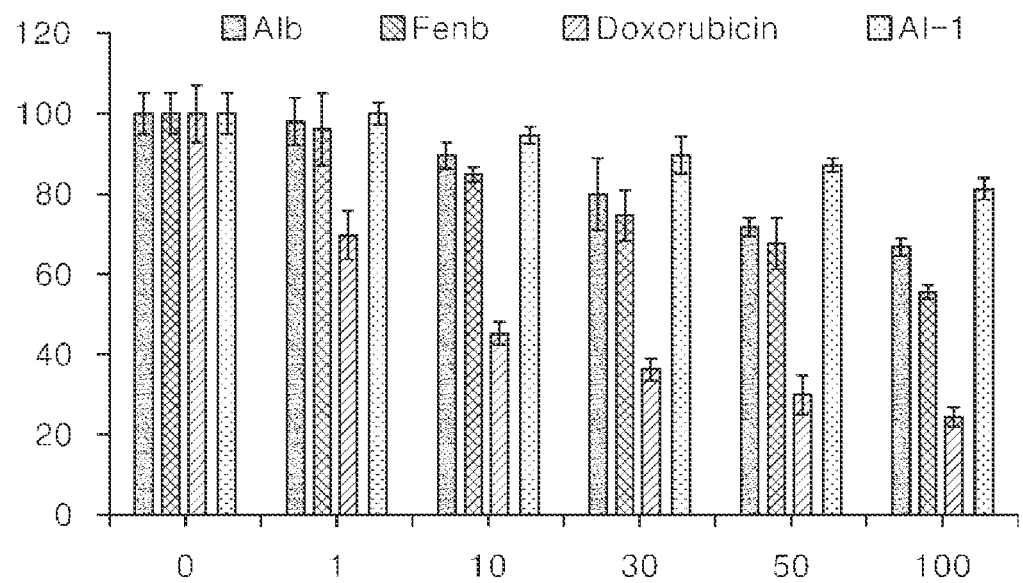
FIG. 2 is a graph showing a result of a toxicity test in normal cell lines according to an embodiment of the present invention.

FIG. 2 illustrates the result of the toxicity test in the normal cell lines. As can be seen in FIG. 2, it can be seen that the toxicity of the albendazole-sugar compound (AL-1) to the normal cell lines is very weak compared to albendazole, fenbendazole, and doxorubicin. Therefore, since the albendazole-sugar compound (AL-1) has very excellent growth inhibition efficiency of cancer cell lines and almost exhibits no toxicity to normal cells, it can be confirmed that the albendazole-sugar compound (AL-1) selectively exhibits an anti-cancer effect by targeting only the cancer cells.

Table 3 shows a relative evaluation of the results of the cancer cell line growth inhibition test and the normal cell line toxicity test of the 4 types of benzimidazole carbamate-sugar compound conjugate compounds prepared according to Examples compared to doxorubicin.

TABLE 3

|  | Cancer Cell line growth inhibition test | Normal cell line toxicity test |
|---|---|---|
| Albendazole-1,2,3,4-β-D-glucose (AL-1) | AA | AA |
| Albendazole-1,2,3,4-β-D-fructose (AL-2) | AA | AA |
| Fenbendazole-1,2,3,4-β-D-glucose (FB-1) | AA | AA |
| Fenbendazole-1,2,3,4-β-D-fructose (FB-2) | AA | AA |

In Table 3 above, a first column represents a cancer cell line growth inhibition test compared to doxorubicin, wherein AA represents equal (1 to 2 times), A represents slightly weak (3 to 5 times), B represents weak (5 to 10 times), and C represents very weak (10 times or more). A second column represents a toxicity test for normal cell lines compared to doxorubicin, wherein AA represents little toxicity (1/10 times), A represents slightly toxic (1/3 times or less), and B represents similar toxicity (1 to 2 times) and C represents high toxicity (10 times or more).

As the results of the cancer cell line growth inhibition test and the normal cell line toxicity test in Table 3 above, it was confirmed that the benzimidazole carbamate-sugar compound conjugate compounds according to the present invention had very excellent cancer cell growth inhibitory activity, and very low toxicity in the normal cell line toxicity test. Accordingly, it can be seen that the benzimidazole carbamate-sugar compound conjugate compounds according to the present invention selectively exhibit an anti-cancer effect by targeting only the cancer cells.

As described above, specific embodiments of the novel benzimidazole derivatives according to the present invention, the preparation method thereof, and the use as the anti-cancer agent using the same have been described, but it is obvious that various modifications can be made without departing from the scope of the present invention.

Therefore, the scope of the present invention should not be limited to the embodiments and should be defined by the appended claims and equivalents to the appended claims. In other words, the embodiments described above are illustrative in all aspects and should be understood as not being restrictive, and the scope of the present invention is represented by appended claims to be described below rather than the detailed description, and it is to be interpreted that the meaning and scope of the appended claims and all changed or modified forms derived from the equivalents thereof are included within the scope of the present invention.

What is claimed is:

1. A benzimidazole carbamate-sugar compound conjugate compound represented by the following Chemical Formula 1:

[Chemical Formula 1]

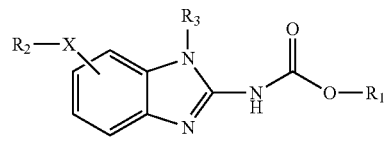

wherein, $R_1$ is a sugar-compound residue, wherein the sugar compound is selected from tetrose aldose, pentose aldose, hexose aldose, tetrose ketose, pentose ketose, hexose ketose, their oxides (CHO is converted to —COOH), deoxy derivatives (—OH is converted to —H), amino sugars (—OH is converted to —NH), glycosides, disaccharides or polysaccharides thereof, $R_2$ and $R_3$ are the same as or different from each other and represent hydrogen, a substituted hydrocarbon group, an alkyl group having 1 to 10 carbon atoms, or an aryl group or a heteroaryl group having 3 to 10 ring atoms, wherein the alkyl group, aryl group, or heteroaryl group is substituted with a substituent selected from halogen, cyano, hydroxy, thiol, amino, alkyl, alkyloxy, alkylamino, dialkylamino, aryl, aryloxy, arylamino, diarylamino or heteroaryl groups, and X is selected from the group consisting of —O—, —S—, —SO—, —SO$_2$—, —NH—, —N(R$_2$)—, —CH$_2$—, —CH(R$_2$)—, and —CO—.

2. The benzimidazole carbamate-sugar compound conjugate compound of claim 1, wherein the benzimidazole carbamate-sugar compound conjugate compound is selected from a compound represented by the following Chemical Formula 2:

[Chemical Formula 2]

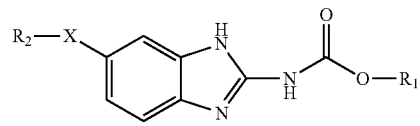

wherein, $R_1$, $R_2$ and X are the same as those defined in Chemical Formula 1.

3. The benzimidazole carbamate-sugar compound conjugate compound of claim 2, wherein a

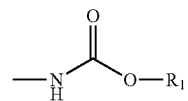

moiety in Chemical Formula 2 has one of the following structures:

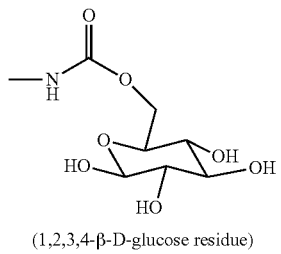

(1,2,3,4-β-D-glucose residue)

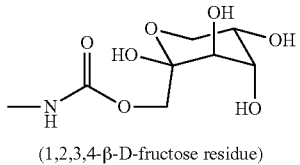

(1,2,3,4-β-D-fructose residue)

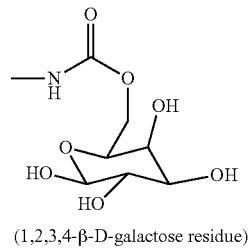

(1,2,3,4-β-D-galactose residue)

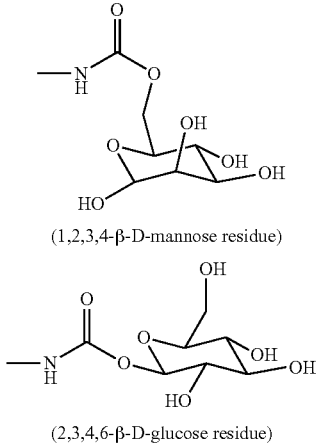

(1,2,3,4-β-D-mannose residue)

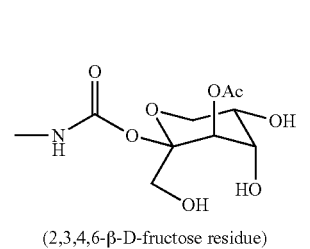

(2,3,4,6-β-D-glucose residue)

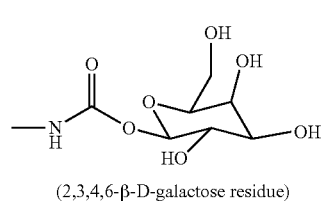

(2,3,4,6-β-D-fructose residue)

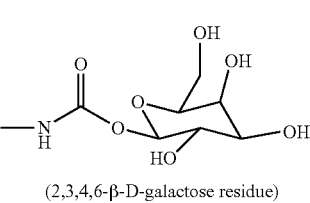

(2,3,4,6-β-D-galactose residue)

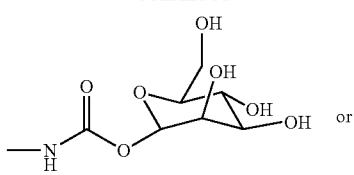

(2,3,4,6-β-D-mannose residue) or

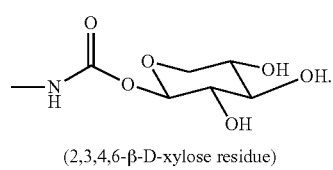

(2,3,4,6-β-D-xylose residue)

4. The benzimidazole carbamate-sugar compound conjugate compound of claim 2, wherein a benzimidazole moiety in Chemical Formula 2 has one of the following structures:

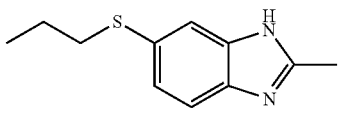

(2-carbamate-removed albendazole residue)

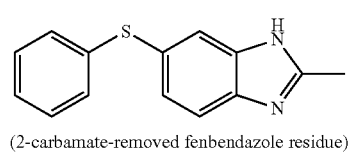

(2-carbamate-removed fenbendazole residue)

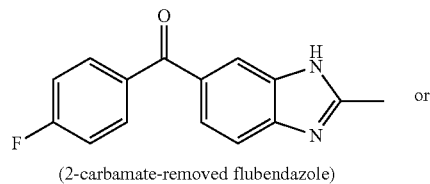

(2-carbamate-removed flubendazole) or

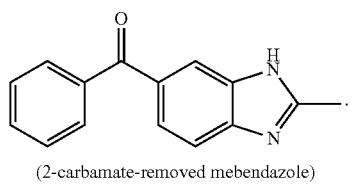

(2-carbamate-removed mebendazole)

5. The benzimidazole carbamate-sugar compound conjugate compound of claim 1, wherein a

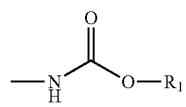

moiety in Chemical Formula 1 has one of the following structures:

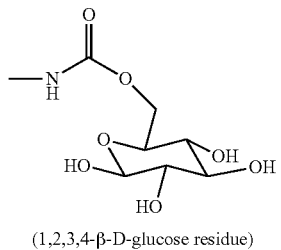
(1,2,3,4-β-D-glucose residue)

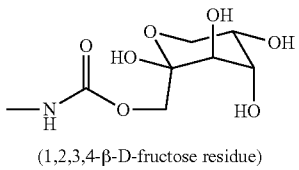
(1,2,3,4-β-D-fructose residue)

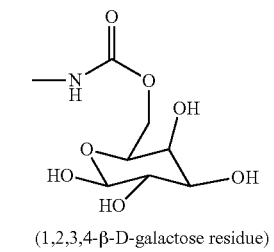
(1,2,3,4-β-D-galactose residue)

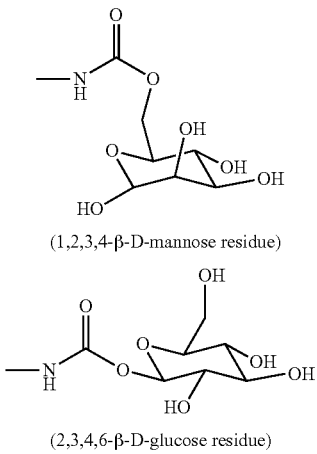
(1,2,3,4-β-D-mannose residue)

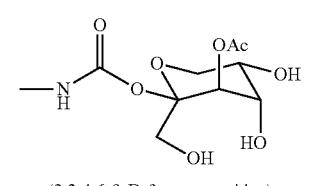
(2,3,4,6-β-D-glucose residue)

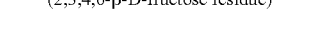
(2,3,4,6-β-D-fructose residue)

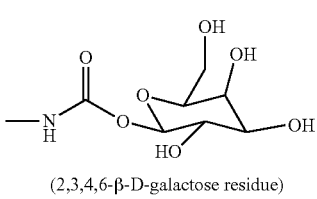
(2,3,4,6-β-D-galactose residue)

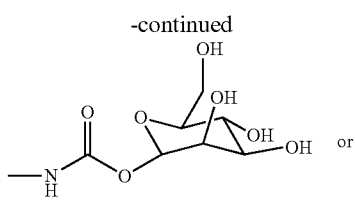
(2,3,4,6-β-D-mannose residue) or

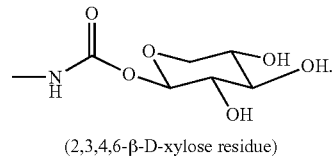
(2,3,4,6-β-D-xylose residue)

6. The benzimidazole carbamate-sugar compound conjugate compound of claim 1, wherein a benzimidazole moiety in Chemical Formula 1 has one of the following structures:

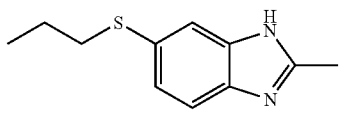
(2-carbamate-removed albendazole residue)

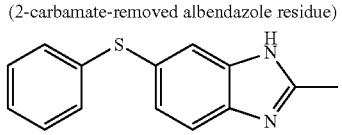
(2-carbamate-removed fenbendazole residue)

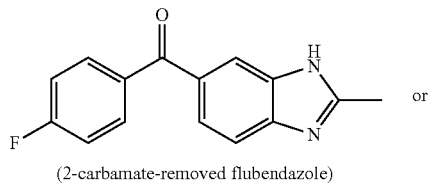
(2-carbamate-removed flubendazole) or

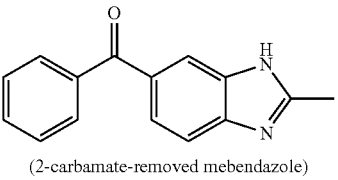
(2-carbamate-removed mebendazole).

7. The benzimidazole carbamate-sugar compound conjugate compound of claim 1, wherein the benzimidazole carbamate-sugar compound conjugate compound is at least one selected from the group consisting of:

as an albendazole-D-sugar compound conjugate compound, Albendazole-1,2,3,4-β-D-glucose, Albendazole-1,2,3,4-β-D-fructose, Albendazole-1,2,3,4-β-D-galactose, Albendazole-1,2,3,4-β-D-mannose, Albendazole-2,3,4,6-β-D-glucose, Albendazole-2,3,4, 6-β-D-fructose, Albendazole-2,3,4,6-β-D-galactose, Albendazole-2,3,4,6-β-D-mannose, Albendazole-2,3,4, 6-β-D-xylose;

as a fenbendazole-D-sugar compound conjugate compound, Fenbendazole-1,2,3,4-β-D-glucose, Fenbendazole-1,2,3,4-β-D-fructose, Fenbendazole-1,2,3,4-β-D-galactose, Fenbendazole-1,2,3,4-β-D-mannose, Fenbendazole-2,3,4,6-β-D-glucose, Fenbendazole-2,3,4,6-β-D-fructose, Fenbendazole-2,3,4,6-β-D-galactose, Fenbendazole-2,3,4,6-β-D-mannose, Fenbendazole-2,3,4,6-β-D-xylose;

as a flubendazole-D-sugar compound conjugate compound, Flubendazole-1,2,3,4-β-D-glucose, Flubendazole-1,2,3,4-β-D-fructose, Flubendazole-1,2,3,4-β-D-galactose, Flubendazole-1,2,3,4-β-D-mannose, Flubendazole-2,3,4,6-β-D-glucose, Flubendazole-2,3,4,6-β-D-fructose, Flubendazole-2,3,4,6-β-D-galactose, Flubendazole-2,3,4,6-β-D-mannose, Flubendazole-2,3,4,6-β-D-xylose; and as a mebendazole-D-sugar compound conjugate compound, Mebendazole-1,2,3,4-β-D-glucose, Mebendazole-1,2,3,4-β-D-fructose, Mebendazole-1,2,3,4-β-D-galactose, Mebendazole-1,2,3,4-β-D-mannose, Mebendazole-2,3,4,6-β-D-glucose, Mebendazole-2,3,4,6-β-D-fructose, Mebendazole-2,3,4,6-β-D-galactose, Mebendazole-2,3,4,6-β-D-mannose, Mebendazole-2,3,4,6-β-D-xylose.

8. A pharmaceutical composition comprising the benzimidazole carbamate-sugar compound conjugate compound according to claim 1 to exhibit anti-cancer activity.

9. The pharmaceutical composition of claim 8, wherein the compound is absorbed through a glucose transporter (GLUT) channel.

10. The pharmaceutical composition of claim 8, wherein the compound inhibits the formation of microtubules and inhibits the absorption of sugar compounds.

11. A preparation method of a benzimidazole carbamate-sugar compound conjugate compound represented by the following Chemical Formula 1, by reacting and binding a primary alcohol group (—OH) of a sugar compound to a benzimidazole carbamate compound of the following Chemical Formula 1a:

[Chemical Formula 1]

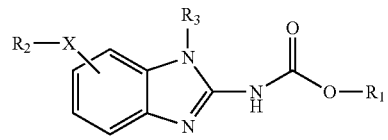

[Chemical Formula 1a]

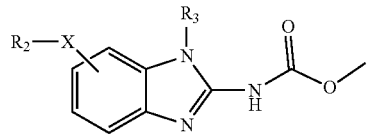

wherein, $R_1$ is a sugar-compound residue, wherein the sugar compound is selected from tetrose aldose, pentose aldose, hexose aldose, tetrose ketose, pentose ketose, hexose ketose, their oxides (CHO is converted to —COOH), deoxy derivatives (—OH is converted to —H), amino sugars (—OH is converted to —NH), glycosides, disaccharides or polysaccharides thereof, $R_2$ and $R_3$ are the same as or different from each other and represent hydrogen or a substituted hydrocarbon group, an alkyl group having 1 to 10 carbon atoms, or an aryl group or a heteroaryl group having 3 to 10 ring atoms, wherein the alkyl group, aryl group, or heteroaryl group is substituted with a substituent selected from halogen, cyano, hydroxy, thiol, amino, alkyl, alkyloxy, alkylamino, dialkylamino, aryl, aryloxy, arylamino, diarylamino or heteroaryl groups, and X is selected from the group consisting of —O—, —S—, —SO—, $—SO_2—$, —NH—, $—N(R_2)—$, $—CH_2—$, $—CH(R_2)—$, and —CO—.

* * * * *